(12) United States Patent
Wu et al.

(10) Patent No.: US 6,682,898 B2
(45) Date of Patent: Jan. 27, 2004

(54) HIGH-THROUGHPUT SCREENING ASSAYS FOR MODULATORS OF STAT4 ACTIVITY

(75) Inventors: Pengguang Wu, San Bruno, CA (US); Judi McKinney, Palo Alto, CA (US)

(73) Assignee: Tularik Inc., So. San Francisco, CA (US)

( * ) Notice: Subject to any disclaimer, the term of this patent is extended or adjusted under 35 U.S.C. 154(b) by 268 days.

(21) Appl. No.: 09/818,094

(22) Filed: Mar. 26, 2001

(65) Prior Publication Data

US 2002/0039749 A1 Apr. 4, 2002

Related U.S. Application Data

(62) Division of application No. 09/053,003, filed on Mar. 31, 1998, now Pat. No. 6,207,391.

(51) Int. Cl.[7] .................... G01N 33/53; G01N 33/566
(52) U.S. Cl. .............. 435/7.1; 435/7.8; 436/501; 436/518; 436/537; 436/542; 436/540
(58) Field of Search .................. 436/501, 518, 436/537, 540, 542; 435/7.1, 7.8

(56) References Cited

U.S. PATENT DOCUMENTS

| 5,591,825 A | 1/1997 | McKnight et al. |
| 5,639,858 A | 6/1997 | Hoey et al. |
| 5,710,266 A | 1/1998 | McKnight et al. |

OTHER PUBLICATIONS

Schlessinger, J., "SH2/SH3 signaling proteins" *Cur. Opin. in Gen. and Dev.,* 4:25–30 (1994).
Pawson, T. "Protein modules and signaling networks" *Nature,* 373:573–580 (1995).
Kaplan, M.H. et al., "Stat6 is required for mediating responses to IL–4 and for the development of Th2 cells" *Immunity,* 4:313–319 (1996).
"The Jak–STAT Mechanism of Signal Transduction" *The Cytokine Bulletin,* pp. 1–6 (1995).
"Stat Sampler Kit" *The 1998 Online Antibody Catalog,* Transduction Laboratories, 5 pages (Mar. 29, 1998).
"STAT Antibodies" *Research Diagnostics,* pp. 1–9 (Mar. 26, 1998).
Darnell et al., *Science,* 264:1415 (1994).
Ihle et al., *Trends Biochem. Sci,* 19:222 (1994).
Ihle et al., *Trends Genetics,* 11:69 (1995).
Shuai et al., *Nature,* 366:580 (1993).
Kaplan et al., *Nature,* 382:174–177 (1996).
Thierfelder et al., *Nature,* 382:171–174 (1996).
Hou et al., *Science,* 265:1701–1706 (1994).
Quelle et al., *Mol. Cell. Biol.,* 15:3336–3343 (1995).
Yamamoto et al., *Cytogenet Cell. Genet.,* 77:207–210 (1997).
Zhong et al., *Proc. Nat'l Acad. Sci USA,* 91:4806–4810 (1994).
Carpenter, *FASEB J.,* 6:3283–3289 (1992).
Myers et al, *Trends in Biochem. Sci,* 19:289–293 (1994).
Schindler, C., "Transcriptional Responses to Polypeptide Ligands: The JAK–STAT Pathway" *Annual Review of Biochemistry,* 64:621–651, Figure 1: p. 627 and second pull paragraph on p. 641 (1995).
Wang et al., "IL–4 Function Can Be Transferred to the IL–2 Receptor by Tyrosine Containing Sequence Found in the IL–4 Receptor alpha Chain" *Immunity,* 4:113–121 (1996).
Ryan et al., "Growth and Gene Expression Are Predominantly Controlled by Distinct Regions of the Humna IL–4 Receptor" *Immunity,* 4:123–132, Figure 8: p. 130 (1996).

*Primary Examiner*—John Ulm
(74) *Attorney, Agent, or Firm*—Townsend and Townsend and Crew LLP

(57) ABSTRACT

This invention provides receptor peptides that have a high affinity for STAT4 and STAT6 polypeptides. Also provided are assays that are useful for identifying compounds that modulate the interaction between STAT4 and STAT6 polypeptides and their respective cellular promoters. The assays are amenable to high throughput screening.

21 Claims, 6 Drawing Sheets

US 6,682,898 B2

HIGH-THROUGHPUT SCREENING ASSAYS FOR MODULATORS OF STAT4 ACTIVITY

BACKGROUND OF THE INVENTION

1. Field of the Invention

This invention pertains to the field of high throughput assays for identifying modulators of interactions between the signal transducer and activator of transcription molecules STAT4 and STAT6 and their corresponding receptors.

2. Background

The growth, differentiation, and functional responses of many cells are controlled by cytokines, growth factors, and hormones. While many of these responses are desirable for normal development of an organism, or to help an organism fight an attacking pathogenic organism or a disease condition, in other situations the cellular response to a given stimulus is inappropriate. For example, T helper cells are an integral part of an organism's defense against harmful antigens. However, when produced at art inappropriate time, T helper cells can attack the organism itself, thus resulting in an autoimmune disease. In other situations, it may be desirable to trigger or enhance a particular response, even in the absence of the usual stimulatory signal.

Development of methods by which one can influence the response of a cell to a given cytokine or growth factor stimulus would be facilitated by an understanding of the signal transduction pathway by which an interaction between a cell and a cytokine is translated into a response by the cell. Generally, cytokines bind to a cell surface receptor of the cytokine receptor superfamily. Binding of a cytokine to its corresponding receptor causes receptor aggregation as well as association of a Janus protein tyrosine kinase (Jaks) with the receptor. Receptor aggregation allows the Jaks to transphosphorylate each other, which dramatically increases their catalytic activity. The activated Jaks then phosphorylate the receptor. Also phosphorylated by the activated Jaks is a polypeptide that is responsible for transmitting the signal to the cell's nucleus. These polypeptides are members of a family of proteins known as *Signal transducers and activators of transcription* (STAT; Darnell et al. (1994) *Science* 264: 1415; for review, see, e.g., Ihle et al. (1994) *Trends Biochem. Sci.* 19: 222; Ihle et al. (1995) *Trends Genetics* 11: 69). STATs are activated by contact with the phosphorylated receptor; activation results in the STAT polypeptides forming a dimer and entering the nucleus, where the STAT dimer binds to the regulatory region of a gene that is inducible by the particular cytokine. Binding of the activated STAT dimer triggers transcription of the gene.

Seven STAT polypeptides are known (STAT1, STAT2, STAT4, STAT5a, STAT5b, and STAT6); these polypeptides have molecular masses from 84–113 kDa. Each STAT protein contains a Src homology-2 (SH2) domain capable of recognizing one or more phosphotyrosine sequences in the cytoplasmic portion of the activated receptor (Shuai et al. (1993) *Nature* 366: 580). Each cytokine receptor is specific for a particular STAT protein, and each STAT activates transcription of certain genes, thus providing two layers of cytokine specificity.

At least two of the STAT polypeptides, STAT4 and STAT6, are intimately involved in regulation of immune responses. STAT4 transduces to the nucleus signals from the IL-12 receptor. IL-12 is involved in the development of a $T_H1$ immune response (Kaplan et al. (1996) *Nature* 382: 174–177), which is part of an organism's defense against intracellular pathogens. IL-12 is also necessary for the T-cell-independent induction of the cytokine interferon (IFN)-γ, which is a key step in the initial suppression of bacterial and parasitic infections. Knockout mice which lack STAT4 were found to be defective in all IL-12 functions tested, including the induction of IFN-gamma, mitogenesis, enhancement of natural killer cytolytic function and $T_H1$ differentiation (Thierfelder et al. (1996) *Nature* 382: 171–174).

IL-4 signals are transduced to the nucleus by STAT6. IL-4 is a key cytokine in the initiation of a $T_H2$ immune response, and also activates B and T lymphocytes. STAT6-deficient mice were deficient in IL-4 activities (Kaplan et al. (1996) *Immunity* 4: 313–319; Takeda et al. (1996) *Nature* 380: 627–630; Shimoda et al. (1996) *Nature* 380: 630–633).

Because of the importance of STAT4 and STAT6 in modulating the immune response of an organism, both in response to infection and in undesirable conditions such as inflammation, allergic reactions, and autoimmune diseases, a need exists by which the clinician can enhance or reduce STAT4 and STAT6 signals. Intervention at the STAT level would have significant advantages compared to previous approaches, which typically target the IL-4 or IL-12 cytokine itself, or the interaction of the cytokine with the receptor. Disruption of cytokine function itself can cause a variety of undesirable side effects. These can be avoided by intervening at the level of STAT-mediated signal transduction. However, identification of agents that can modulate STAT4 and STAT6-mediated signal transduction has been hampered by the lack of suitable assays. Assay of binding of STAT4 and STAT6 to their corresponding receptors, and identification of agents which increase or decrease the degree of such binding, has been difficult because of the high rate at which the STAT4 and STAT6 polypeptides bind to ($k_{on}$) and leave the receptor ($k_{off}$) after initial binding. The present invention fulfils this need for effective assays by which modulators of STAT4 and STAT6 binding can be identified, as well as other needs.

SUMMARY OF THE INVENTION

The invention provides receptor peptides that have a high affinity for STAT6 polypeptides, and thus are useful in assays to identify modulators of STAT6 binding to corresponding receptors. The peptides include an amino acid sequence YX$_1$X$_2$X$_3$ (SEQ ID NO:1), wherein X$_1$ is selected from the group consisting of K, V, R, I, M, a nonnatural amino acid such as tert-butyl glycine, norvaline, cyclohexylalanine, or allothreonine; X$_2$ is selected from the group consisting of P, A and S, and X$_3$ is selected from the group consisting of W, Y, F, H, L and an aromatic normatural amino acid. Suitable aromatic nonnatural amino acids include, for example, p-iodophenylalanine, 1-napthylalanine, benzothiophenylalanine, 3-iodotyrosine, p-chlorophenylalanine, m-trifluoromethylphenylalanine, and o-chlorophenylalanine. In preferred embodiments, the peptide does not include the amino acid sequence YKPF (SEQ ID NO:2). Also provided are STAT6 receptor peptides of the invention in which the tyrosine is phosphorylated; such phosphorylated receptor peptides bind to STAT6 with high affinity.

In another embodiment, the invention provides receptor peptides that have a high affinity for STAT4 polypeptides. These peptides include an amino acid sequence GYLPZ$_3$NID (SEQ ID NO:3), wherein Z$_3$ is selected from the group consisting of Q, H, N, and W; other STAT4 receptor peptides include the amino acid sequence GYDMPHVL (SEQ ID NO:4). Peptides having the tyrosine phosphorylated are also provided, these STAT4 receptor peptides are capable of binding to STAT4 with high affinity.

Another embodiment of the invention provides methods of screening for modulators of STAT6 binding to a STAT6 receptor. The methods involve incubating a reaction mixture comprising a STAT6 polypeptide, a potential binding modulator, and a STAT6 receptor peptide as set forth herein. The amount of binding of the STAT6 polypeptide to the receptor polypeptide is determined and is typically compared to the amount of binding observed in an assay which lacks the potential binding modulator in order to determine whether the potential binding modulator increases or decreases binding of the STAT6 polypeptide to the receptor peptide.

The invention also provides methods of screening for compounds that modulate STAT4 binding to a STAT6 receptor. These methods involve incubating a reaction mixture comprising a STAT4 polypeptide, a potential binding modulator, and a receptor peptide which comprises an amino acid sequence GYDMPHVL (SEQ ID NO:4) or GYLPZ$_3$NID (SEQ ID NO:3), wherein the tyrosine is phosphorylated and Z$_3$ is selected from the group consisting of Q, H, N, and W. One then determines whether the binding of the STAT4 polypeptide to the receptor peptide is increased or decreased in comparison to an assay which lacks the potential binding modulator.

DETAILED DESCRIPTION

Definitions

Figure 1:
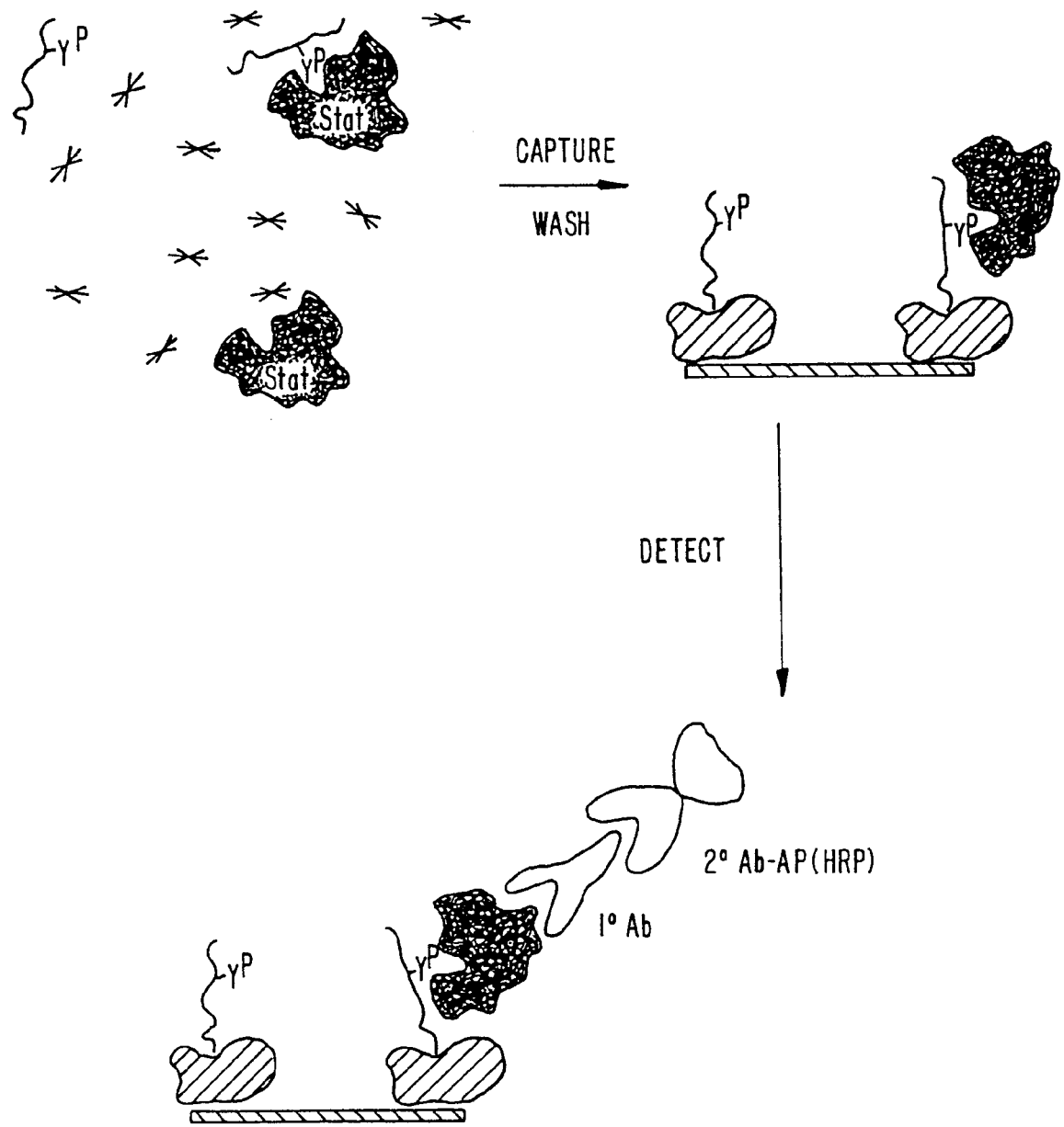
FIG. 1 shows a schematic diagram of a chemiluminescence assay for determining the effect of a potential activity modulator (*) on binding of a STAT polypeptide to a receptor peptide that includes a phosphotyrosine residue ($Y^P$). The receptor peptide is immobilized on a solid support and the amount of STAT polypeptide bound to the receptor peptide is determined by binding to the STAT polypeptide a primary antibody (1° Ab) to which is bound a labeled secondary antibody (2° Ab-AP(HRP)).

The following terms are expressly defined for purposes of this application.

A "detectable moiety" or "label" is a composition that is detectable, either directly or indirectly, by spectroscopic, photochemical, biochemical, immunochemical, or chemical means. For example, useful labels include $^{32}$p, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

A "modulator of STAT protein-receptor binding" is a compound that increases or decreases the ability of a STAT polypeptide to bind to a corresponding receptor peptide in a selected system. A "potential modulator of STAT protein-receptor binding" is a compound that is to be assessed for the ability to increase or decrease binding of a STAT polypeptide to a corresponding receptor peptide in a selected system. Samples or assays that are treated with a potential modulator are compared to control samples without the test compound, to examine the extent of inhibition or activation of STAT polypeptide binding. Control samples (untreated with test inhibitors or activators) are assigned a relative STAT polypeptide binding value of 100. Inhibition of STAT polypeptide binding is achieved when the binding activity value of the test sample relative to the control is about 75, preferably 50, more preferably 25. Activation is achieved when the binding activity value of the test sample relative to the control is about 150, more preferably 200.

Description of the Preferred Embodiments

The present invention provides reagents and methods for identifying compounds which can modulate the ability of STAT polypeptides, in particular STAT4 and STAT6, to interact with their corresponding receptors. The methods are efficient and readily amenable to high-throughput drug screening protocols, as gel separation steps are avoided. High-throughput screening (HTS) methods, compositions, kits and integrated systems for performing the assays are also provided. In general, the assays are performed by incubating a potential binding modulator with a STAT polypeptide and a receptor peptide that is capable of binding the STAT polypeptide in the absence of a binding modulator. The invention provides specific receptor peptides for STAT4 and STAT6.

The invention represents an improvement over existing technology for determining STAT polypeptide binding activity in several ways. For example, (a) previously available assays were hampered by the lack of receptor peptides that have a sufficient affinity for STAT4 and STAT6 polypeptides to enable highly sensitive assays; (b) the assays of the invention do not require the use of radioactive reagents (although they are optionally used as discussed below); (c) gel separations steps are entirely avoided; (d) each of the formats described is readily amenable for automation and high throughput screening ("HTS") using current reagents, devices and methodologies. The method steps can be repeated in parallel in a microtiter plate format, for example, thus allowing one to screen at least about 1,000–100,000 different potential activity modulators for an effect on STAT binding in a single day.

Agents that modulate interactions between STAT polypeptides and their receptors have value for in vitro modulation of STAT polypeptide-receptor binding, e.g., as tools for studying the mechanisms of signal transduction, for controlling gene expression in the production of recombinant polypeptides, and the like. More importantly, these modulators provide lead compounds for drug development for a variety of conditions, including treatment of autoimmune diseases, allergic reactions, asthma, and other conditions that involve cellular responses to growth factors, cytokines, and hormones. Accordingly, the assays are of immediate value for their ability to identify lead compounds for pharmaceutical or other applications.

Indeed, because STAT6 in particular is involved in transducing to the nucleus a signal generated by binding of IL-4 to its cell surface receptor, STAT6 plays a central role in modulating immune responses that involve activation of B and T lymphocytes, and differentiation of $T_H2$ cells. Therefore, modulation of STAT6 activity is useful in prevention and treatment of immunological diseases such as allergy, asthma, anaphylaxis, atopic dermatitis, and the like. STAT4 is also involved in signal transduction, in this case transmitting to the nucleus a signal which results from binding of IL-12 or interferon-α to the IL-12 receptor. Thus, modulators of STAT4 find use in, for example, treatment of conditions that involve expression of interferon-γ (e.g., autoimmune diseases, multiple sclerosis, diabetes mellitus, rheumatoid arthritis, and the like), enhancement of natural killer cytolytic function, and differentiation of $T_H1$ cells (e.g., defenses against intracellularpathogens). The range of conditions to which modulators of STAT4 and STAT6 polypeptide binding includes conditions in humans and other animals.

STAT4 and STAT6 Receptor Peptides

The invention provides receptor peptides that exhibit enhanced binding affinity for the STAT4 and STAT6 polypeptides relative to the native receptors with which these STAT polypeptides interact. The receptor peptides of the invention are useful, for example, in screening assays for identifying compounds that are capable of modulating interactions between STAT4 and STAT6 and their respective receptor counterparts. Both STAT4 and STAT6 binding requires the presence of a phosphorylated tyrosine residue within the receptor peptide.

The receptor peptides of the invention have a higher binding affinity for the corresponding STAT4 or STAT6 protein than does a native receptor or a region of a native receptor that corresponds to the amino acid sequence of the receptor peptide. For example, the receptor peptides of the invention are typically capable of inhibiting the binding of STAT4 to an IL-12 receptor or STAT6 to an IL-4 receptor with an $IC_{50}$ that is at least about two-fold less than the $IC_{50}$ of a receptor peptide having an amino acid sequence derived from a natural receptor. More preferably, the receptor peptide $IC_{50}$ is at least about three-fold less, still more preferably at least about five-fold less than that of a peptide having an amino acid sequence derived from a natural receptor for a STAT polypeptide. An $IC_{50}$ measurement can be determined from the concentration of phosphorylated receptor peptide required to achieve 50% binding to a corresponding STAT polypeptide. Low concentration (or low $IC_{50}$) indicates high affinity of the receptor peptide for the STAT polypeptide.

The STAT4 and STAT6 receptor peptides can be prepared standard chemical peptide synthesis techniques. Where the desired subsequences are relatively short, the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield, et al. *J. Am. Chem. Soc.,* 85: 2149–2156 (1963), and Stewart et al., *Solid Phase Peptide Synthesis,* 2nd ed., Pierce Chem. Co., Rockford, Ill. (1984).

Alternatively, the STAT4 and STAT6 receptor peptides can be prepared using recombinant methods. Generally this involves creating a DNA sequence that encodes the receptor peptide, placing the DNA in an expression cassette under the control of a particular promoter, expressing the receptor peptide in a host, isolating the expressed receptor peptide and, if required, renaturing the peptide. Because the receptor peptides of the invention typically are not found in nature, recombinant production generally involves synthesis of a nucleic acid that encodes the receptor peptide. DNA encoding the receptor peptides of this invention can be prepared by any suitable method as described above, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences. Alternatively, subsequences can be cloned and the appropriate subsequences cleaved using appropriate restriction enzymes. The fragments can then be ligated to produce the desired DNA sequence.

The nucleic acid sequences encoding the receptor peptides can be expressed in a variety of host cells, including *E. coli,* other bacterial hosts, yeast, and various higher eukaryotic cells such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. The recombinant receptor peptide gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the receptor peptides can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., in the assays described herein).

The STAT4 and STAT6 receptor peptides of the invention can include additional amino acids and other chemical groups in addition to the amino acid sequences set forth above. For example, the receptor peptides can include additional amino acids at either or both ends of the specified amino acid sequences. In the case of STAT4 receptor peptides, for example, these additional amino acids can correspond to those found in the phosphotyrosine-containing SH2 region of a native IL-12 receptor to which STAT4 binds. For STAT6, the additional amino acids at one or both ends of the receptor peptide can correspond to those found in the phosphotyrosine-containing SH2 region of a native IL-4 receptor to which STAT4 binds Alternatively, either or both ends of the specified amino acid sequence can be flanked by additional amino acids that are not found at the corresponding positions in the native receptor. The invention also provides STAT4 and STAT6 receptor peptides that are linked to a tag or epitope that is useful for, e.g., immobilization or detection when the receptor peptide is used in the assays for STAT4 or STAT6 binding that are provided by the invention. Receptor peptides having such tags, and methods for their preparation, are discussed below.

Although the term "peptide" is used herein in reference to the receptor peptides, it is noted that the use of this term does not limit the invention to peptides of any particular maximum length. Thus, the term "receptor peptide" includes polypeptides and proteins which include the amino acid sequences specified herein.

STAT4 Receptor Peptides.

In one embodiment, the invention provides receptor peptides that are capable of specifically binding to STAT4. These isolated peptides include the amino acid sequences GYLDMPHVL (SEQ ID NO:16) or GYLPZ$_3$NID (SEQ ID NO:3), wherein Z$_3$ is selected from the group consisting of Q, H, N, and W. Also provided are receptor peptides in which the tyrosine is phosphorylated; such peptides of the invention can bind to STAT4. Preferred STAT4 receptor peptides include those which include an amino acid sequence YLPZ$_3$N (SEQ ID NO:14) or GYLPZ$_3$ (SEQ ID NO:15); examples of preferred peptides are those which include an amino acid sequence selected from the group consisting of GYDMPHVL (SEQ ID NO:4), GYLPZ$_3$NID (SEQ ID NO:3), EGYVPWQDLI (SEQ ID NO:17), SHEGYLPQNID (SEQ ID NO:18), SHEGYLPHNID (SEQ ID NO:19), SHEGYLPNNID (SEQ ID NO:20), and SHEGYLPWNID (SEQ ID NO:21). Binding affinities for some of the preferred STAT4 receptor peptides, and for a peptide derived from the SH2 domain of the IL-12 receptor to which STAT4 binds, are shown in Table 1.

TABLE 1

STAT4 Receptor Peptides

| RECEPTOR PEPTIDE | BINDING AFFINITY | SEQ ID NO: |
|---|---|---|
| SHEGY$^P$LPSNID (IL-12 receptor) | 2.9 μM | 22 |
| SHEGY$^P$LPQNID | 0.39 μM | 23 |
| SHEGY$^P$LPHNID | 0.70 μM | 24 |
| SHEGY$^P$LPNNID | 0.51 μM | 25 |
| SHEGY$^P$LPWNID | 0.93 μM | 26 |

Y$^P$ = phosphorylated tyrosine.

STAT6 Receptor Peptides.

In other embodiments, the invention provides receptor peptides that are capable of specifically binding to STAT6. The STAT6 receptor peptides typically include the amino acid sequence YX$_1$X$_2$X$_3$ (SEQ ID NO:27), wherein:

X$_1$ is selected from the group consisting of K, V, R, I, M, and a first nonnatural amino acid;

X$_2$ is selected from the group consisting of P, A and S; and

X$_3$ is selected from the group consisting of W, Y, F, H, L and an aromatic second nonnatural amino acid.

In preferred embodiments, the peptide does not include the amino acid sequence YKPF (SEQ ID NO:2). Also provided by the invention are STAT6 receptor peptides in which the tyrosine is phosphorylated; such receptor peptides can bind to STAT6 polypeptides.

Suitable aromatic nonnatural amino acids for use as X$_3$ include, for example, p-iodophenylalanine, 1-napthylalanine, benzothiophenylalanine, 3-iodotyrosine, p-chlorophenylalanine, o-trifluoromethylphenylalanine, and o-chlorophenylalanine. Preferably, X$_3$ is W or Y. In other preferred embodiments, when X$_1$ is K, X$_3$ is an aromatic nonnatural amino acid.

Nonnatural amino acids that are suitable for use as X$_1$ include, for example, of tert-butyl glycine, norvaline, cyclohexylalanine, and allothreonine.

The STAT6 receptor peptides of the invention also include those which include the amino acid sequence YX$_1$X$_2$X$_3$ (SEQ ID NO:28), in which only one or two of X$_1$, X$_2$ and X$_3$ is an optimal residue as set forth above. Thus, the invention includes peptides in which X$_1$ is selected from the group consisting of K, V, R, I, M, tert-butyl glycine, norvaline, cyclohexylalanine, and allothreonine; X$_2$ is any amino acid, and X$_3$ is selected from the group consisting of W, Y, H, F, and L. Suitable STAT6 receptor peptides also include those which include the amino acid sequence YX$_1$X$_2$X$_3$ (SEQ ID NO:29), in which X$_1$ is any amino acid except G or P, X$_2$ is any amino acid, and X$_3$ is selected from the group consisting of W, Y, F, H, and L.

In preferred embodiments, the STAT6 receptor peptides include the amino acid sequence YX$_1$X$_2$X$_3$X$_4$ (SEQ ID NO:30), in which X$_1$, X$_2$, and X$_3$ are as set forth for SEQ ID NO:1, above, and X$_4$ is selected from the group consisting of D and G.

Preferred STAT6 receptor peptides of the invention include the amino acid sequences EGYVPWQDLI (SEQ ID NO:17), EGYKPZ$_1$QDLI (SEQ ID NO:31), and EGYZ$_2$PQWDLI (SEQ ID NO:32), wherein Z$_1$ is an aromatic nonnatural amino acid as set forth above and Z$_2$ is a nonnatural amino acid selected from the group consisting of tert-butyl glycine, norvaline, cyclohexylalanine, and allothreonine. Other preferred STAT6 receptor peptides include Ac-YVPW-NH$_2$ (SEQ ID NO:33) and Ac-YVPWQ-NH$_2$ (SEQ ID NO:34), where Ac is an acetyl group and NH$_2$ is an amide-linked group. Attachment of acetyl and amide groups is preferred for shorter (i.e., 4–5 amino acid) receptor peptides; these group function as protecting groups. Other protecting groups known to those of skill in the art can be substituted for the acetyl and amide groups.

Binding affinities for some of the preferred STAT6 receptor peptides, and for a peptide derived from the SH2 domain of the IL-4 receptor to which STAT6 binds, are shown in Table 2.

TABLE 2

STAT6 Receptor Peptides

| RECEPTOR PEPTIDE | BINDING AFFINITY | SEQ ID NO: |
|---|---|---|
| ASSGEEGY$^P$KPFQDLI | 3.3 μM | 5 |
| ASSGEEGYKPFQDLI (IL-4 receptor amino acids 624–638) | | |
| Ac-Y$^P$KPF-NH2 | 22 μM | 35 |
| Ac-Y$^P$VPW-NH2 | 1.2 μM | 36 |
| Ac-Y$^P$VPWQ-NH2 | 1.5 μM | 37 |
| EGY$^P$VPWQDLI | 0.61 μM | 38 |

$Y^P$ = phosphorylated tyrosine.

Assays for STAT4 and STAT6 Binding

The invention also provides assays for identifying compounds that modulate the interaction between the STAT4 and STAT6 polypeptides and their corresponding receptors. The assay methods involve incubating a reaction mixture that includes a receptor peptide for the particular STAT polypeptide of interest, a potential modulator of binding between the receptor peptide and the STAT polypeptide, and determining whether the binding of the STAT polypeptide to the receptor peptide is increased or decreased in comparison to an assay which lacks the potential binding modulator.

STAT4 assays typically employ a STAT4 receptor peptide such as those described above. For example, the receptor peptides typically include the amino acid sequence GYLD-MPHVL (SEQ ID NO:16) or GYLPZ$_3$NID (SEQ ID NO:3), wherein $Z_3$ is selected from the group consisting of Q, H, N, and W in which the tyrosine is phosphorylated. In preferred embodiments, the assays use a STAT4 receptor peptide that includes an amino acid sequence YLPZ$_3$N (SEQ ID NO:14) or GYLPZ$_3$ (SEQ ID NO:15); examples of preferred peptides for use in the assays are those which include an amino acid sequence selected from the group consisting of GYD-MPHVL (SEQ ID NO:4), GYLPZ$_3$NID (SEQ ID NO:3), EGYVPWQDLI (SEQ ID NO:17), SHEGYLPQNID (SEQ ID NO:18), SHEGYLPHNID (SEQ ID NO:19), SHEGYLP-NNID (SEQ ID NO:20), and SHEGYLPWNID (SEQ ID NO:21).

The STAT6 assays typically employ a STAT6 receptor peptide as described above. These receptor peptides typically include an amino acid sequence YX$_1$X$_2$X$_3$ (SEQ ID NO:1), wherein the tyrosine is phosphorylated and:

$X_1$ is selected from the group consisting of K, V, R, I, M, and a first nonnatural amino acid;

$X_2$ is selected from the group consisting of P, A and S; and $X_3$ is selected from the group consisting of W, Y, F, H, L and an aromatic second nonnatural amino acid. In preferred embodiments, the STAT6 receptor peptide used in the assay does not include the amino acid sequence YKPF (SEQ ID NO:2). In other preferred embodiments, when $X_1$ is K, $X_3$ is an aromatic nonnatural amino acid.

Suitable first nonnatural amino acids for use as $X_1$ include, for example, tert-butyl glycine, norvaline, cyclohexylalanine, and allothreonine. For use as $X_3$, suitable aromatic second nonnatural amino acids p-iodophenylalanine, 1-napthylalanine, benzothiophenylalanine, 3-iodotyrosine, p-chlorophenylalanine, m-trifluoromethylphenylalanine, and o-chlorophenylalanine.

The receptor peptide can comprise an amino acid sequence YX$_1$X$_2$X$_3$X$_4$ (SEQ ID NO:30), wherein $X_4$ is selected from the group consisting of D and G, and $X_1$, $X_2$ and $X_3$ are as set forth for SEQ ID NO:1, above. In preferred embodiments, the STAT6 binding assays employ a receptor peptide that includes an amino acid sequence selected from the group consisting of EGYVPWQDLI (SEQ ID NO: 17), EGYKPZ$_1$QDLI (SEQ ID NO:39), and EGYZ$_2$PQWDLI (SEQ ID NO:32), wherein: $Z_1$ is an aromatic nonnatural amino acid selected from the group consisting of p-iodophenylalanine, 1-napthylalanine, benzothiophenylalanine, 3-iodotyrosine, p-chlorophenylalanine, m-trifluoromethylphenylalanine, and o-chlorophenylalanine; and $Z_2$ is a nonnatural amino acid is selected from the group consisting of tert-butyl glycine, norvaline, cyclohexylalanine, and allothreonine.

The STAT4 and STAT6 polypeptides to be used in the assays of the invention can be purified from a natural source or may be recombinantly produced, and are usually provided in at least a partially-purified form, although the assays can function when provided with a crude cell lysate that contains a STAT polypeptide. In a preferred embodiment, the STAT polypeptides are synthesized using recombinant DNA methodology. Generally this involves creating a DNA sequence that encodes the STAT polypeptide, modified as desired, placing the DNA in an expression cassette under the control of a particular promoter, expressing the protein in a host, isolating the expressed protein and, if required, renaturing the protein. STAT4- and STAT6-encoding nucleic acids that are useful for recombinant production of STAT polypeptides for use in the assays of the invention, and methods of obtaining such nucleic acids, are known to those of skill in the art. For example, human STAT6-encoding nucleic acids and the corresponding polypeptides are described in U.S. Pat. No. 5,591,825; see also, Hou et al. (1994) *Science* 265: 1701–1706. STAT6 nucleic acids and polypeptides from other organisms are also known (see, e.g. Quelle et al. (1995) *Mol. Cell. Biol.* 15: 3336–3343 (mouse cDNA sequence). STAT4 nucleic acids are also known in the art (see, e.g., Yamamoto et al. (1997) *Cytogenet. Cell Genet.* 77: 207–210 (human), Zhong et al. (1994) *Proc. Nat'l. Acad. Sci. USA* 91: 4806–4810 (mouse). STAT-encoding nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science,* 241: 1077–1080; Van Brunt (1990) *Biotechnology,* 8: 291–294; Wu and Wallace, (1989) Gene, 4: 560; and Barringer et al. (1990) *Gene* 89: 117.

DNA encoding the STAT polypeptides and the receptor peptides can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066. In one preferred embodiment, a nucleic acid encoding a STAT4 or STAT6 polypeptide can be isolated by routine cloning methods. A nucleotide sequence of a STAT4 or STAT6 gene as provided in, for example, GenBank or other sequence database can be used to provide probes that specifically hybridize to a STAT gene in a genomic DNA sample, or to a STAT mRNA in a total RNA sample (e.g., in a Southern or Northern blot). Once the target STAT nucleic acid is identified, it can be isolated according to standard methods known to those of skill in the art (see, e.g., Sambrook et al. (1989) *Molecular Cloning: A Laboratory Manual, 2nd Ed., Vols.* 1–3, Cold Spring Harbor Laboratory; Berger and Kimmel (1987) *Methods in Enzymology, Vol.* 152: *Guide to Molecular Cloning Techniques,* San Diego: Academic Press, Inc.; or Ausubel et al. (1987) *Current Protocols in Molecular Biology,* Greene Publishing and Wiley-Interscience, New York).

STAT4 and STAT6 polypeptides can be expressed in a variety of host cells as discussed above, including *E. coli,* other bacterial hosts, yeast, and various higher eukaryotic cells such as the COS, CHO and HeLa cells lines and myeloma cell lines. As is the case for recombinant expression of receptor peptides described above, the recombinant STAT polypeptide gene will be operably linked to appropriate expression control sequences for each host. Transformation, expression, and purification methods such as those discussed above for receptor peptides are likewise suitable for recombinant expression of STAT4 and STAT6 polypeptides.

Occasionally only a portion of a native STAT4 or STAT6 polypeptide is used in the assay, the portion being sufficient for binding to the corresponding receptor peptide with an affinity of preferably not less than an order of magnitude less than that of the full-length STAT4 or STAT6 polypeptide. Portions capable of imparting the requisite binding specificity and affinity are readily identified by those skilled in the art. A wide variety of molecular and biochemical methods are available for generating catalytic fragments of a STAT polypeptide.

The assay mixture can also include a variety of other reagents, such as salts, buffers, neutral proteins, e.g., albumin, detergents, and the like, which may be used to facilitate optimal protein-protein binding and/or reduce non-specific or background interactions, etc. Reagents that otherwise improve the efficiency of the assay, such as protease inhibitors, nuclease inhibitors, antimicrobial agents, and the like, can also be used.

The assay mixtures are incubated under conditions in which the STAT4 or STAT6 polypeptide can selectively bind to the receptor peptide, if not for the presence of the potential binding modulator compound. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 1 and 10 hours, preferably less than 5 hours, more preferably less than 2 hours. For optimal high throughput applications, the reaction is carried out for between 0.1 and 4 hours, more typically between about 0.5 and 1.5 hours.

After incubation, the presence or absence of selective binding between the STAT4 or STAT6 polypeptide and the corresponding receptor peptide is detected by any convenient way. Often, a separation step is used to separate bound from unbound components. The separation step may be accomplished in a variety of ways. Conveniently, at least one of the components is immobilized on a solid substrate which may be any solid from which the unbound components may be conveniently separated. For example, either the receptor peptide or the STAT polypeptide can be immobilized on a solid support. Immobilization can occur before, during, or after the incubation with the corresponding binding molecule.

Conveniently, the assay component to be immobilized can include a tag that mediates binding of the component to the solid support. The tag can be any of a variety of components. In general, a molecule which binds the tag (a tag binder) is fixed to a solid support, and the tagged STAT polypeptide or receptor peptide is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. See, Id. Indeed, the antibody can be either the tag or the tag binder, or antibodies can be used as both tags and tag binders. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as, e.g., transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook,* Academic Press New York, and Hulme (ed) *Receptor Ligand Interactions A Practical Approach,* Rickwood and Hames (series editors) Hulme (ed) IRL Press at Oxford Press NY). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Specific tag-tag binder interactions occur when the tag and tag binder bind with a $K_D$ of at least about 0.01 μM, preferably at least about 0.001 μM or better, and most typically and preferably, 0.0001 μM or better, under standard assay conditions.

Methods for the attachment of tags to peptides are known to those of skill in the art. In one preferred embodiment, preparation of a tagged assay component involves producing a fusion protein by recombinant methods. For example, a polynucleotide encoding the STAT polypeptide or the receptor peptide is operably linked to a polynucleotide that encodes an epitope for which convenient means of detection exist. The polynucleotide encoding the epitope is preferably placed at a location relative to the assay component coding sequence that does not disrupt the ability of the fusion protein to bind to its corresponding target. Methods for constructing and expressing genes that encode fusion proteins are well known to those of skill in the art. Examples of these techniques and instructions sufficient to direct persons of skill through many cloning exercises are found in Berger, Sambrook, and Ausubel, supra. Examples of suitable epitopes include the myc and V-5 reporter genes; expression vectors useful for recombinant production of recognition reagents having these epitopes are commercially available (e.g., Invitrogen (Carlsbad Calif.) vectors pcDNA3.1/Myc-His and pcDNA3.1 V5-His are suitable for expression in mammalian cells). Additional expression vectors for suitable fusion proteins, and corresponding detection systems are known to those of skill in the art, and several are commercially available (e.g., FLAG™ (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" *In Genetic Engineering: Principles and Methods,* J. K. Setlow, Ed., Plenum Press, NY; commercially available from Qiagen (Santa Clarita, Calif.)).

Other haptens that are suitable for use as tags are known to those of skill in the art and are described, for example, in the *Handbook of Fluorescent Probes and Research Chemicals* ($6^{th}$ Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, the hapten includes a thiol, a heterobifunctional linker such as SMCC can be used to attach the tag to lysine residues present on the recognition moiety.

Tag binders are fixed to solid substrates using any of a variety of methods currently available. Solid substrates are commonly derivitized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield (1963) *J. Am. Chem. Soc.* 85: 2149–2154 (describing solid phase synthesis of, e.g., peptides); Geysen et al. (1987) *J. Immun. Meth.* 102: 259–274 (describing synthesis of solid phase components on pins). See, Frank and Doring (1988) *Tetrahedron* 44: 6031–6040 (describing synthesis of various peptide sequences on cellulose disks); Fodor et al. (1991) *Science* 251: 767–777; Sheldon et al. (1993) *Clinical Chemistry* 39(4): 718–719 and Kozal et al. (1996) *Nature Medicine* 2(7): 753–759 (all describing arrays of biopolymers fixed to solid substrates). Non-chemical approaches for fixing tag binders to substrates include other common methods, such as heat, cross-linking by UV radiation, and the like.

Solid supports suitable for use in the binding assays of the invention are known to those of skill in the art. As used herein, a solid support is a matrix of material in a substantially fixed arrangement. Exemplar solid supports include glasses, plastics, polymers, metals, metalloids, ceramics, organics, etc. Solid supports can be flat or planar, or can have substantially different conformations. For example, the substrate can exist as particles, beads, strands, precipitates, gels, sheets, tubing, spheres, containers, capillaries, pads, slices, films, plates, dipsticks, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.). The substrate is chosen to maximize signal to noise ratios, primarily to minimize background binding, for ease of washing and cost.

Separation can be effected for example, by removing a bead or dipstick from a reservoir, emptying or diluting a reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc.

Detection can be effected in any convenient way. Frequently, one of the components comprises or is coupled to a label. For example, where the STAT polypeptide is immobilized on the solid support, the receptor peptide can be coupled to a label. Conversely, where the receptor peptide is immobilized, the corresponding STAT polypeptide can be labeled. The assay component can be either directly labeled, i.e., comprise or react to produce a detectable label, or indirectly labeled, i.e., bind to a molecule comprising or reacting to produce a detectable-label. For indirect labeling, the moiety to which the label is attached and which binds to the STAT polypeptide or the receptor peptide is termed a "detection moiety." Labels can be directly attached to or incorporated into the assay component or detection moiety by chemical or recombinant methods.

In one embodiment of a detection moiety, a label is coupled to a molecule, such as an antibody comprising a recognition domain for an assay component, through a chemical linker. Antibodies specific for both STAT4 and STAT6 polypeptides are commercially available (e.g., Transduction Laboratories, Lexington Ky.; Santa Cruz Biotech, Santa Cruz Calif.). Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the recognition domain. In one embodiment, the flexible linker is an amino acid subsequence comprising a proline such as Gly(x)-Pro-Gly(x) (SEQ ID NO:40) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection moiety or to the STAT polypeptide or receptor peptide, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry,* 2nd ed., Springer Verlag, NY and in Haugland (1996) *Handbook of Fluorescent Probes and Research Chemicals,* a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^{3}$H, $^{125}$I, $^{35}$s, $^{14}$c, $^{32}$p, $^{33}$p, etc.), enzymes (eg., horse radish peroxidase, alkaline phosphatase etc.), spectral calorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions. In certain assay formats of the invention, alkaline phosphatase is not suitable for use as a label because the phosphatase can dephosphorylate the tyrosine residue of the receptor peptide, thus eliminating its ability to bind to the corresponding STAT polypeptide. However, in assay formats in which the phosphorylated tyrosine is sterically protected, e.g., receptor peptide immobilized, alkaline phosphatase can be used.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., β-galactosidase, luciferase, and horse radish peroxidase. The chemiluminescent substrate for luciferase is luciferin. One embodiment of a chemiluminescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Most typically, binding of STAT polypeptides to the corresponding receptor peptide is measured by quantitating the amount of label fixed to the solid support by binding of the detection reagent. Typically, presence of a modulator during incubation will increase or decrease the amount of label fixed to the solid support relative to a control incubation which does not comprise the modulator, or as compared to a baseline established for a particular assay type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Methods for Reducing Background in Immunoassays

The invention also provides methods by which increased sensitivity can be achieved in immunoassays such as those used to study STAT polypeptide interactions with their receptors. The assays of the invention provide a high throughput method of screening for inhibitors of protein domain interactions with peptide ligands where the protein domain has a high on/off rate and as such is not well suited to a 96-well (or larger) format for screening. With a high on/off rate, during the wash steps commonly conducted in standard immunoassays, the protein of interest will tend to get removed from the assay during a wash step. The assay methods of the invention increase the signal to noise ratio by at least two fold over similar assays that do not employ the invention. The signal to noise reduction can be determined in comparison to an assay conducted by standard ELISA procedures and including wash steps in between additions. Standard solution binding assays, or ELISAs can be conducted as described in standard protocol books or as obtained in commercially available kits.

The assays of the invention can be conducted as an ELISA assay, using a 96-well microplate format or a larger format if desired. In one embodiment, a phosphotyrosine-containing receptor peptide is incubated with a protein which contains an SH2 domain (e.g., a STAT polypeptide) to provide opportunity for the SH2 domain containing protein to bind the peptide. The peptide is preferably bound to a tag, e.g., biotin, at the amino terminus of the peptide. There can be a spacer between the tag and the peptide. The solution is placed in wells of a 96-well microplate that are coated with a tag binder, e.g., streptavidin. Reduction of background is achieved by incubating, in a separate reaction, a primary antibody specific for the SH2 domain containing protein and a secondary antibody specific for the first antibody which is to bind to the SH2 domain containing protein. The secondary antibody has conjugated to it a substrate for detection. The antibodies bind and form a binding pair of antibodies Ab1 and Ab2. Ab1 remains available to bind the SH2 domain containing protein for which it is specific. Ab2 remains conjugated to a substrate for chemiluminescence detection later.

The solution containing binding pairs of primary and secondary antibodies bound together is then added to the microwells that already contain the bound streptavidin, biotinylated receptor peptide and an SH2 domain containing protein bound to the receptor peptide. The pair of antibodies binds the SH2 domain containing protein bound to the peptide, and a standard chemiluminescence reaction occurs with either alkaline phosphatase detection, or horse radish peroxidase detection. The concentration of the SH2 domain containing protein that is required to achieve 50% binding with the native phosphotyrosine peptide ligand provides a point of comparison for the relative binding affinities of the pairs that are tested. Where the assay is used to screen inhibitors of the protein-peptide interaction, the absence of a signal indicates a positive inhibitor.

An alternate method for conducting the assay involves preincubating the SH2 domain containing protein with the primary antibody that is specific for the SH2 domain containing protein. A biotinylated receptor peptide having a phosphotyrosine moiety is placed in a streptavidin coated microwell, and the binding pair which includes the preincubated SH2 domain protein bound to antibody is then added. After allowing time for the SH2-antibody complex to bind the biotinylated peptide bound to streptavidin, a second antibody specific for the first antibody is added, and the presence of the second antibody is detected as before, using a chemiluminescence reaction with either alkaline phosphatase detection or horse radish peroxidase detection. The secondary antibody has a substrate for detection conjugated to it. As before, where the assay is used to screen for inhibitors of the protein-peptide interaction the absence of a signal indicates a positive inhibitor.

Although the above descriptions specify biotin/streptavidin as the tag and tag binder, and STAT polypeptides and receptors, one of skill in the art would appreciate that the methods of the invention are applicable to other tags and to other polypeptide binding pairs.

By preincubating the binding pairs, the nonspecific binding of at least one of the two binding partners is reduced by at least 50% over the nonspecific binding that occurs in the absence of the preincubation of the binding partners. Stated in other words, the background noise that increases in the presence of nonspecific binding, is reduced two fold or better by practicing the method of the invention.

The assay methods of the invention are well suited, for example, in binding assays of SH2 domain containing proteins. SH2 domain containing proteins include e.g. phospholipase Cy (PLCy), RasGTPase-activating protein (RasGAP), Src, Abl, Syk, Csk, PTP I C, p91 of ISGF-3, c-Crk, Grb2, Shc, Nck, p85 of P13-kinase, STAT1, Stat2, Stat3, Stat4, Stat5, and Stat6. SH2 domain containing proteins are easily recognized by a person of ordinary skill in the art (Schlessinger (1994) *J. Curr. Opinion Genet. Devel.* 4:25–30; Carpenter (1992) *FASEB J.* 6: 3283–3289; Myers et al. (1994) *Trends in Biochem. Sci.* 19: 289–293).

The binding of SH2 domains to their target peptides is totally dependent on tyrosine phosphorylation (Schlessinger, supra.; Pawson (1995) Nature 373: 573–579). The SH2 domain proteins bind phosphotyrosine peptide ligands that are ligands of an SH2 domain binding site. These ligands include native receptor phosphotyrosine peptide ligands specific for SH2 domain containing proteins, and other phosphotyrosine containing proteins that can bind an SH2 domain containing protein, e.g. e ligands. Such peptides can be made by standard mutagenesis of DNA sequences encoding the receptor peptides, followed by expression of the mutants. The mutations can consist of single substitutions of amino acid residues along the peptide, e.g. alanine substitutions. The peptides can be chemically or enzymatically phosphorylated for use in the assay.

The phosphotyrosine containing peptide ligands of SH2 domains that bind to their SH2 domain with high affinity bind with dependence on the residues R1 to R3 immediately carboxy to the phosphotyrosine (Schlessinger, supra.; Pawson, supra.). In addition, the peptide binding to the SH2 domain can be influenced by the residues R1 to R4 immediately amino-terminal to the phosphotyrosine moiety (Schlessinger, supra.). As such, a preferred embodiment is a phosphotyrosine containing peptide ligand where the peptide is a native sequence having a total of about 4 to 10 residues, where amino residues R1–R4 are immediately amino-terminal to a phosphotyrosine and the amino-terminus sequence R1–R4 has between one and four residue modifications, each independently comprising a substitution, deletion, or insertion. The carboxy residues R1–R3 of this embodiment can also have between one and three single residue modifications, each independently comprising a substitution, deletion or insertion. A preferred embodiment is a phosphotyrosine-containing peptide ligand having 4 residues where the peptide is a native sequence comprising 3 or fewer modifications comprising single residue substitutions, deletions, or insertions, where the tyrosine is at the amino-most terminal position, and the modifications are at residues R1 to R3 carboxy terminal to the tyrosine position. A more preferred embodiment is such a peptide having 2, most preferably 1 modification comprising a single residue substitution, deletion, or insertion. All peptides can be tested for efficacy by the methods of the invention.

STAT Binding Activity Modulators

The invention also provides methods of identifying compounds that modulate the ability of STAT4 and STAT6 to bind to, and transmit a signal from, their corresponding cell surface receptors. Essentially any chemical compound can be used as a potential binding activity modulator in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g. U.S. Pat. No. 5,539,083), antibody libraries (see, e.g., Vaughn et al., *Nature Biotechnology*, 14(3):309–314 (1996) and PCT/US96/10287), carbohydrate libraries (see, e.g. Liang et al., *Science*, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

As noted, the invention provides in vitro assays for STAT4 and STAT6 binding affinity in a high throughput format. Control reactions that measure the affinity of STAT4 or STAT6 in a reaction that does not include a binding activity modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions which do not include a modulator provide a background level of binding activity.

In some assays it will be desirable to have positive controls to ensure that the components of the assays are working properly. At least two types of positive controls are appropriate. First, a known activator of STAT4 or STAT6 binding can be incubated with one sample of the assay, and the resulting increase in signal resulting from interactions with the corresponding receptor peptides determined according to the methods herein. Second, a known inhibitor of STAT4 or STAT6 binding can be added, and the resulting decrease in affinity similarly detected. It will be appreciated that modulators can also be combined with binding activators or inhibitors to find modulators which inhibit binding activation or repression that is otherwise caused by the presence of the known binding modulator.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (96) modulators. If 1536 well plates are used, then a single plate can easily assay from about 100–about 1500 different compounds. It is possible to assay many different plates per day; assay screens for up to about 6,000–20,000, and even up to about 100,000–1,000,000 different compounds is possible using the integrated systems of the invention.

Compositions, Kits and Integrated Systems

The invention provides compositions, kits and integrated systems for practicing the assays described herein. For example, an assay composition having a STAT4 or STAT6 polypeptide, a corresponding receptor peptide, and a labelling reagent is provided by the present invention. The invention also provides assay compositions for use in the solid phase assays; such compositions can include, for example, a STAT4 or STAT6 polypeptide immobilized on a solid support, a corresponding receptor peptide, and a labelling reagent. In each case, the assay compositions can also include additional reagents that are desirable for STAT binding activity. Modulators of STAT4 and STAT6 binding activity can also be included in the assay compositions.

The invention also provides kits for practicing the STAT4 and STAT6 screening assay methods described above. The kits can include any of the compositions noted above, and optionally further include additional components such as instructions to practice a high-throughput method of assaying for an effect on STAT4 or STAT6 binding, one or more containers or compartments (e.g., to hold STAT4 or STAT6, receptor peptides, or the like), a control binding activity modulator, a robotic armature for mixing kit components or the like.

The invention also provides integrated systems for high-throughput screening of potential modulators for an effect on binding of STAT4 or STAT6 to a receptor. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based computers), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

The following examples are offered to illustrate, but not to limit the present invention.

Example 1

Fast Dissociation of STAT1 Protein from Immobilized Peptide-Biotin

The binding of an interferon-γ receptor-derived peptide sequence GY$^P$DKPHVL (SEQ ID NO:41) to the SH2 domain of STAT1 is relatively tight, with a dissociation constant of about 120 nM. We tested the kinetic properties of the interaction between the peptide and STAT1 protein on a BIAcore 2000 instrument. A biotinylated version of the peptide was immobilized on a streptavidin-coated chip, a solution containing 200 nM STAT1 protein was flowed over the chip at a rate of about 5 μl per minute. 0.1 mg/ml of peptide was used for the immobilization. Bound STAT1 protein was detected by the change in molecule mass (density) on the chip. The binding of STAT1 is very fast, within the borderline of the detection limit. The apparent dissociation of the STAT1-peptide complex is slow. This is due to the rebinding of the dissociated protein since in the presence of excess soluble competing peptide, the dissociation is completed within a few seconds. The association phase is limited by the diffusion of the molecules. In the dissociation phase, the signal is dominated by rebinding since in the excess of soluble competing peptide (30 μM) the dissociation ends very quickly.

Thus, the SH2 domain of STAT1, like many other SH2 domain-containing proteins, binds to peptides with fast association and dissociation kinetics. It would be difficult to retain the bound molecule based solely on the kinetics of dissociation. A prerequisite for the development of an ELISA type of assay with wash steps is therefore the use of a relatively high concentration of peptide such that the bound protein is retained on the plate based on rebinding kinetics. This leads to complications in interpreting experimental data. Thus, the assay is validated by comparing it with another assay based in solution.

Example 2

STAT1 Binding Assay

A STAT1 chemiluminescence assay was conducted as follows (FIG. 1): a 96-well microplate with high protein adsorption capacity was coated with streptavidin overnight at 4° C. at a concentration of 30 μg/ml in 1× PBS buffer (0.15 M NaCl, pH 6.8). After removal of the solution, the plate was blocked with 2% BSA in PBS buffer for one or more hours at room temperature. The plate was then washed and used in the assay. Biotinylated phosphotyrosine peptide and STAT1 protein in the absence or presence of an inhibitor was incubated for 45 to 60 minutes at room temperature. After three washes with water, an anti-STAT1 antibody specific for the C-terminus of the protein mixed with a secondary antibody conjugated to either alkaline phosphatase (AP) or horseradish peroxidase (HRP) was added and incubated for one hour. The plate was then washed to separate the bound from the free antibody complex. A chemiluminescent substrate (CSPD from Tropix, Mass. for alkaline phosphatase or Super Signal luminol solution from Pierce for horseradish peroxidase) was used to detect bound antibody.

A titration with increasing STAT1 protein and a fixed amount of biotinylated peptide indicated that where the peptide concentration is 200 nM, the signal levels off at a STAT1 concentration above 20 nM, and with 100 nM peptide similar results were achieved. The amount of peptide that can be immobilized is limited by the number of streptavidin molecules absorbed on the surface of the well. With too much biotin-peptide, exceeding the amount of immobilized streptavidin, less STAT1 is detected. Thus, the optimal concentration of STAT1 used for the screening reactions was 20 nM.

Example 3

Comparison of Chemiluminescence-based Assay with Fluorescence Polarization

Previous surface-based STAT1 ELISA assays used several washing steps to separate free from bound molecules. Since the association and dissociation of STAT-peptide interaction are very fast, the question arises whether the detected signal is directly related to the amount of bound protein when rebinding kinetics is used to retain bound molecules. To verify that it is, the chemiluminescence-based assay was compared with a fluorescence polarization-based assay. In the fluorescence polarization assay, a fluorescent version of the same STAT1-binding peptide is mixed with STAT1 protein in solution and the change in fluorescence polarization is measured either in a single tube instrument or in a 96-well plate reader. To test whether the two assays produce equivalent results, we compared the competition curves obtained using the unmodified version of the peptide as a competitor. In the fluorescence polarization assay, 20 nM fluorescein-labeled peptide and 100 nM STAT1 protein were used, while in the chemiluminescence assay, 100 mn biotinylated peptide and 20 nM STAT1 protein were used.

With the same competing peptide, the IC50 was about the same in both assays. Thus, even though the absolute amount of bound STAT1 protein may not be measured accurately due to losses in the wash steps, it is possible to obtain a relatively reliable $IC_{50}$ of a competitor in a chemiluminescence-based assay that compared well with the $IC_{50}$ value obtained in a homogenous and more precise assay system. The solid phase chemiluminescence assay is thus capable of faithfully measuring short-lived protein peptide interactions in a microtiter plate format.

Example 4

Optimization of STAT Receptor Peptides

From the sequence of the intracellular portion of the receptor with which the particular SH2 domain containing protein interacts under native conditions, peptides can be designed that have higher affinity for a given protein having an SH2 domain. Such peptides are thus preferred for use in assays for identifying inhibitors of the particular peptide-protein interaction under study. Such modified phosphotyrosine peptide ligands that have higher affinity for the SH2 domain containing protein than the native sequence can be found using the present assay or any standard binding assay. Amino acids of the native peptides are substituted with other amino acids, and the modified peptides are tested for ability to lower the $IC_{50}$ for the SH2 domain containing protein as compared to the $IC_{50}$ with which the native peptide binds the SH2 domain. The $IC_{50}$ can be determined without addition of a competing peptide. The native sequence without modification can be also be used to test for competing peptides.

Table 3 depicts the concentrations of STAT1, STAT4, and STAT6 at 50% binding of the STAT protein to the listed phosphotyrosine peptide ligands.

TABLE 3

$IC_{50}$'s of STAT1, STAT4, and STAT6 with two selected peptides
(Y* = phosphotyrosine)

| peptide | STAT1 | STAT4 | STAT6 | SEQ ID NO: |
|---|---|---|---|---|
| SFGY*DKPHVL | 0.6 μM | 10 μM | >100 μM | 42 |
| ASSGEEGY*KPFQDLI | >100 μM | 30 μM | 3.3 μM | 5 |

The data in Table 3 demonstrates that STAT1 binds SFGY*DKPHVL (SEQ ID NO:42) with high affinity, and STAT6 binds ASSGEEGY*KPFQDLI (SEQ ID NO:5) with high affinity. To design peptide ligands having higher affinity than these sequences, the peptides in the table can be modified systematically by altering the residues immediately carboxy to the tyrosine, e.g. by alanine scan and standard mutagenesis techniques, and testing each peptide in the assay. Thus, the peptides GY*AKPHVL (SEQ ID NO:43), GY*DAPHVL (SEQ ID NO:44), and GY*DKAHVL (SEQ ID NO:45), etc., could be tested for binding affinity.

Example 5

Background Reduction in STAT Binding Assays

This Example demonstrates that background can be reduced, and signal increased, by preincubating certain of the assay components prior to being added to the binding mixture. The data presented in Table 4 demonstrates that the signal to noise ratio for the assay is increased by two-fold or better when the SH2 domain containing proteins STAT1, STAT4, and STAT6 are tested against several phosphotyrosine peptide ligands using the background reduction methods of the invention. The "standard assay" is a standard chemiluminescence assay as depicted in FIG. 1 in which a phosphotyrosine-containing receptor peptide is allowed to bind to the STAT polypeptide. After capture of the receptor peptide and a wash step, a primary antibody against the STAT polypeptide is added. After another wash step, a secondary antibody which binds to the primary antibody is added. In the first alternative embodiment, the STAT polypeptide and the primary antibody are preincubated prior to being added to the assay mixture. In the second alternative embodiment, the primary (Ab1) and secondary (Ab2) antibodies are preincubated prior to addition to the assay mixture.

TABLE 4

Signal to Noise Improvement by Preincubation
(high signal relative to background = + + + +)

|  | GY$^P$DMPHVL (SEQ ID NO:46) | EGY$^P$VPWQDLI (SEQ ID NO:38) |
|---|---|---|
| STAT1 Standard assay | + + | − |
| STAT1 STAT1/Ab preincubation | + + + + | − |
| STAT1 Ab1/Ab2 preincubation | + + + + | − |
| STAT4 Standard assay | + + | − |
| STAT4 STAT4/Ab preincubation | + + + + | − |
| STAT4 Ab1/Ab2 preincubation | + + + + | − |
| STAT6 Standard assay | − | + + |
| STAT6 STAT4/Ab preincubation | − | + + + + + |
| STAT6 Ab1/Ab2 preincubation | − | + + + + + |

Example 6

Binding Assays for Various Proteins which Contain SH2 Domains

This Example describes binding assays for various proteins that contain SH2 domains. The assays make use of phosphotyrosine-containing peptide ligands, as indicated in Table 5 and Table 6.

TABLE 5

Phosphotyrosine-containing peptide ligands specific for SH2 domain-containing proteins (x = any amino acid; +++ = high affinity binding; in each case, Y is phosphotyrosine)

|  | GYDKPHVL (SEQ ID NO:41) | GYKPFQDLI (SEQ ID NO:47) | Y(I/V)NX (SEQ ID NO:48) | Y(L/I)IP (SEQ ID NO:49) | YEEI (SEQ ID NO:50) | YXNX (SEQ ID NO:51) | YIYV (SEQ ID NO:52) | YITPLP (SEQ ID NO:53) |
|---|---|---|---|---|---|---|---|---|
| PLCγ | − | − | − | +++ | − | − | − | +++ |
| Src | − | − | − | − | +++ | − | +++ | − |
| Abl | − | − | − | − | − | − | − | − |
| Syk | − | − | − | − | − | − | − | − |
| Csk | − | − | − | − | − | − | − | − |
| PTP1C | − | − | − | − | − | − | − | − |
| p91 | − | − | − | − | − | − | − | − |
| c-Crk | − | − | − | − | − | − | − | − |
| Grb2 | − | − | +++ | − | − | +++ | − | − |
| Shc | − | − | − | − | − | − | − | − |
| STAT1 | +++ | − | − | − | − | − | − | − |
| STAT2 | − | − | − | − | − | − | − | − |
| STAT3 | − | − | − | − | − | − | − | − |
| STAT4 | ++ | ++ | − | − | − | − | − | − |
| STAT5 | − | − | − | − | − | − | − | − |
| STAT6 | − | +++ | − | − | − | − | − | − |

TABLE 6

Additional phosphotyrosine-containing peptide ligands specific for SH2 domain-containing proteins (x = any amino acid; +++ = high affinity binding; in each case, Y is phosphotyrosine)

|  | YTAVQP (SEQ ID NO:54) | YVPM (SEQ ID NO:55) | YXXL (SEQ ID NO:56) | YMAP (SEQ ID NO:57) | YMNM (SEQ ID NO:58) | YVPM (SEQ ID NO:55) | YMDM (SEQ ID NO:59) | YMXM (SEQ ID NO:60) |
|---|---|---|---|---|---|---|---|---|
| Syp | +++ | − | − | − | − | − | − | − |
| Nck | − | +++ | − | − | − | − | − | − |
| Ras-GAP | − | − | − | +++ | − | − | − | − |
| P85-PI3K | − | − | − | − | +++ | +++ | +++ | +++ |
| Zap70 | − | − | +++ | − | − | − | − | − |

Example 7

Identification of Optimal Receptor Peptides for STAT6

Figure 2:
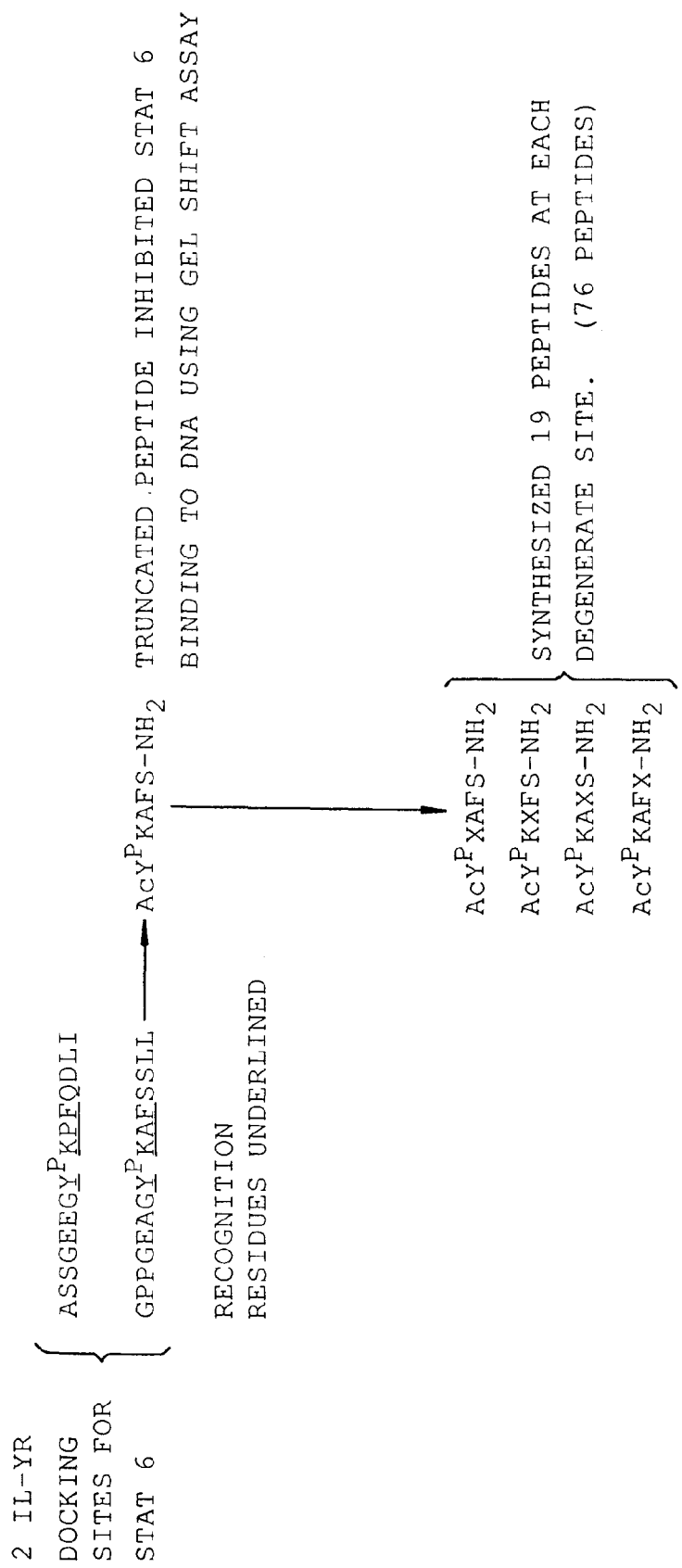
FIG. 2 shows the strategy used to identify optimal receptor peptides for STAT6. Two docking sites for STAT6 which are present in the IL-4 receptor (SEQ ID NOS:5 and 6) were used as the starting point (SEQ ID NO:7). After the four critical recognition residues were identified (underlined), each of the four amino acids which immediately follow the phosphotyrosine were substituted with each of nineteen different amino acids (total of 76 peptides prepared) (SEQ ID NOS:8–11).
Figure 3:
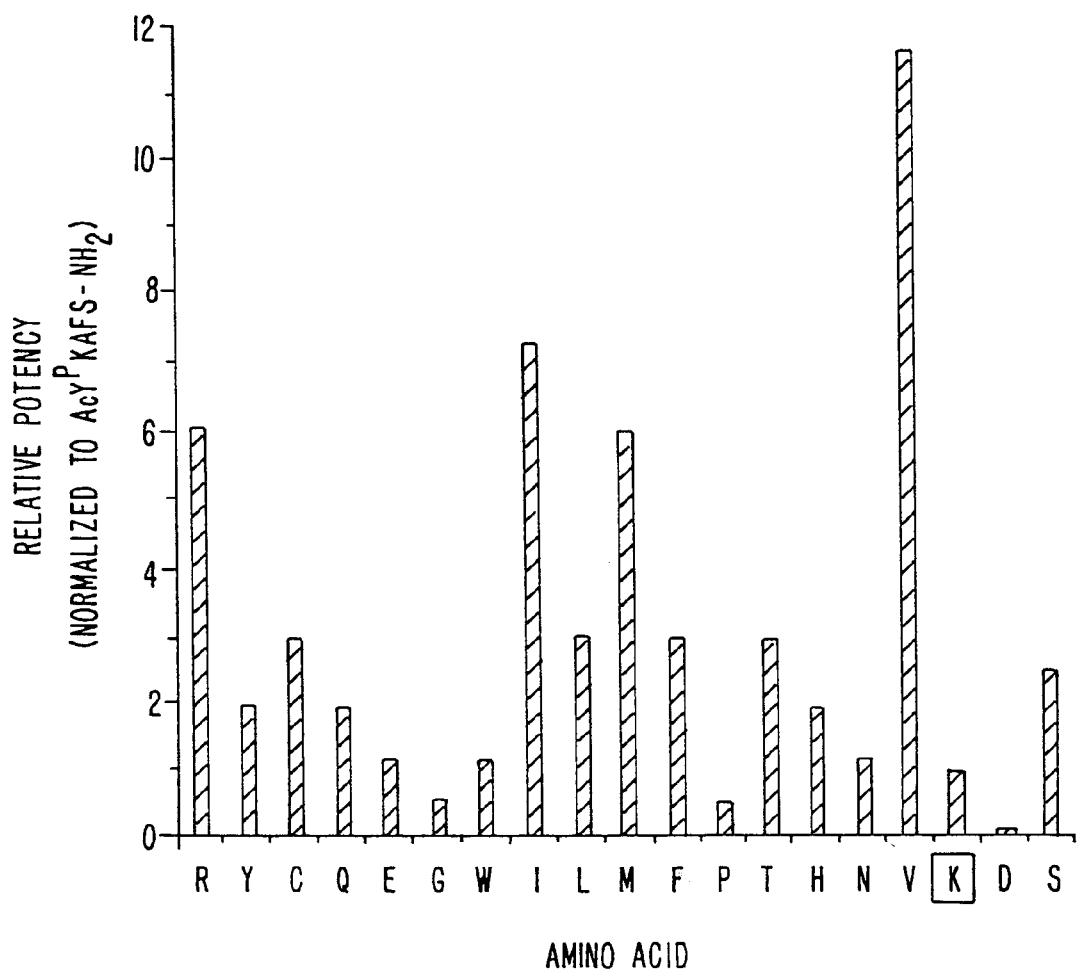
FIG. 3 shows the binding affinity (IC$_{50}$) for peptides having substitutions of the amino acid at the +1 position following the phosphotyrosine (SEQ ID NO:12). Binding potencies are provided relative to that of the naturally occurring amino acid (K) (SEQ ID NO:7).
Figure 4:
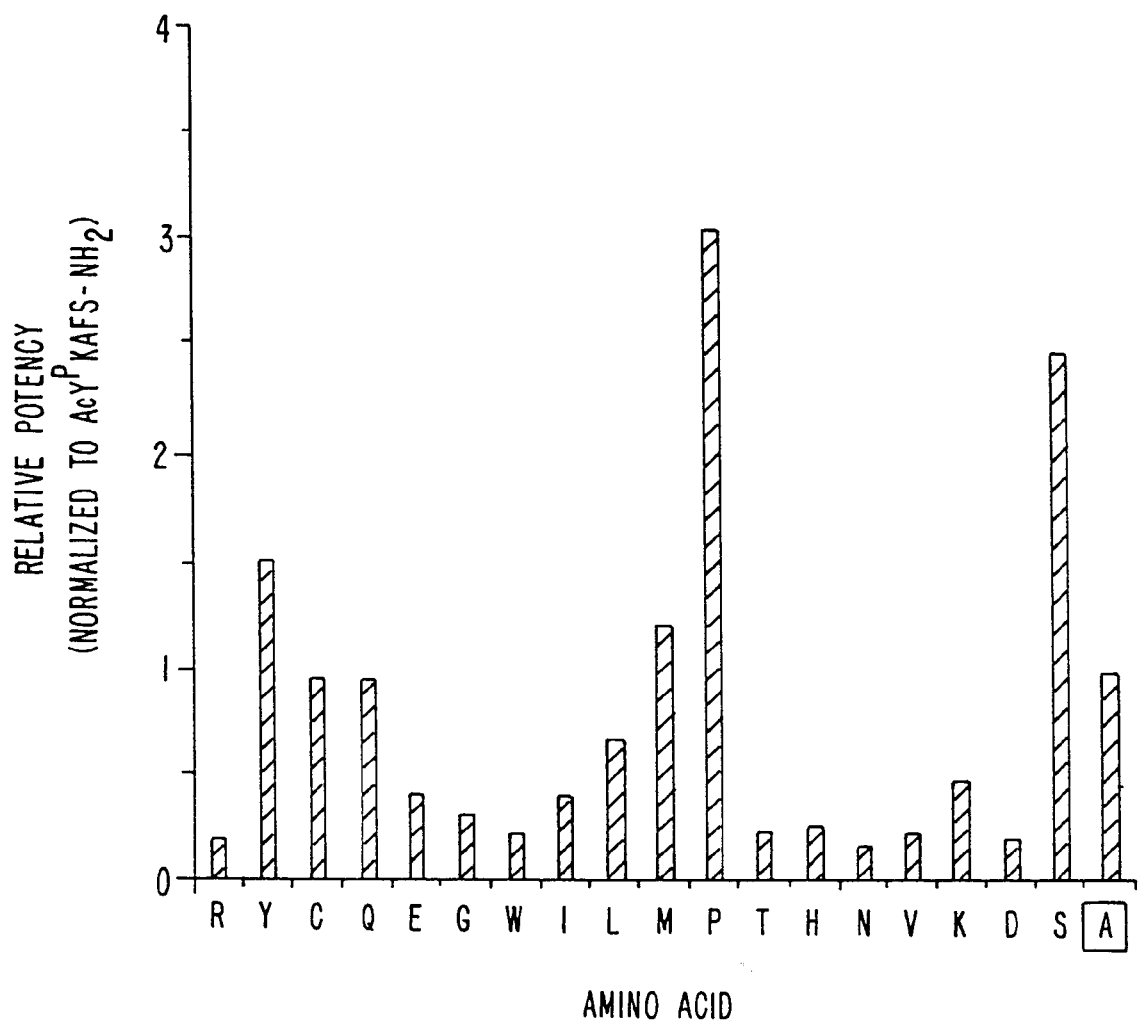
FIG. 4 shows the binding affinity (IC$_{50}$) for peptides having substitutions of the amino acid at the +2 position following the phosphotyrosine (SEQ ID NO:13). Binding potencies are provided relative to that of the naturally occurring amino acid (A) (SEQ ID NO:7).
Figure 5:
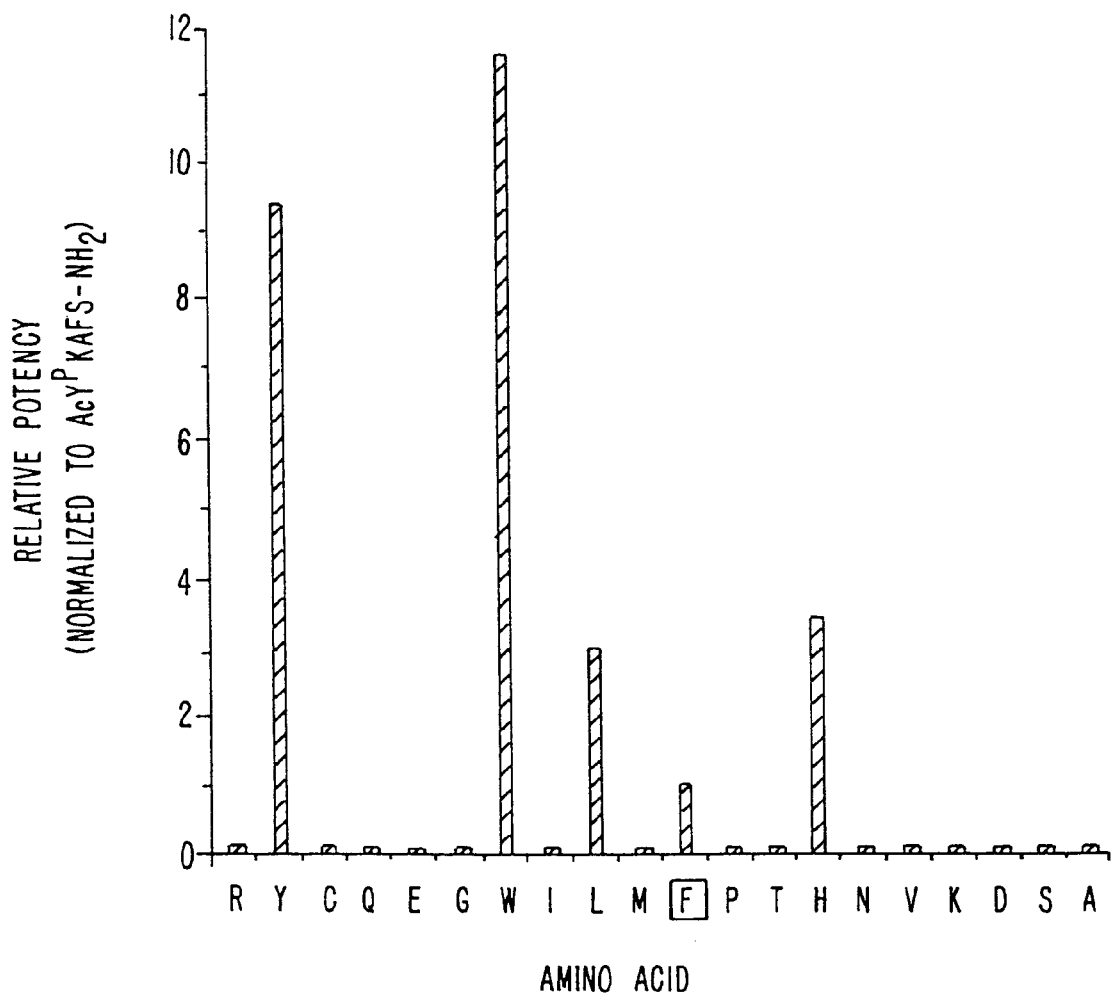
FIG. 5 shows the binding affinity (IC$_{50}$) for peptides having substitutions of the amino acid at the +3 position following the phosphotyrosine (SEQ ID NO:10). Binding potencies are provided relative to that of the naturally occurring amino acid (F) (SEQ ID NO:7).
Figure 6:
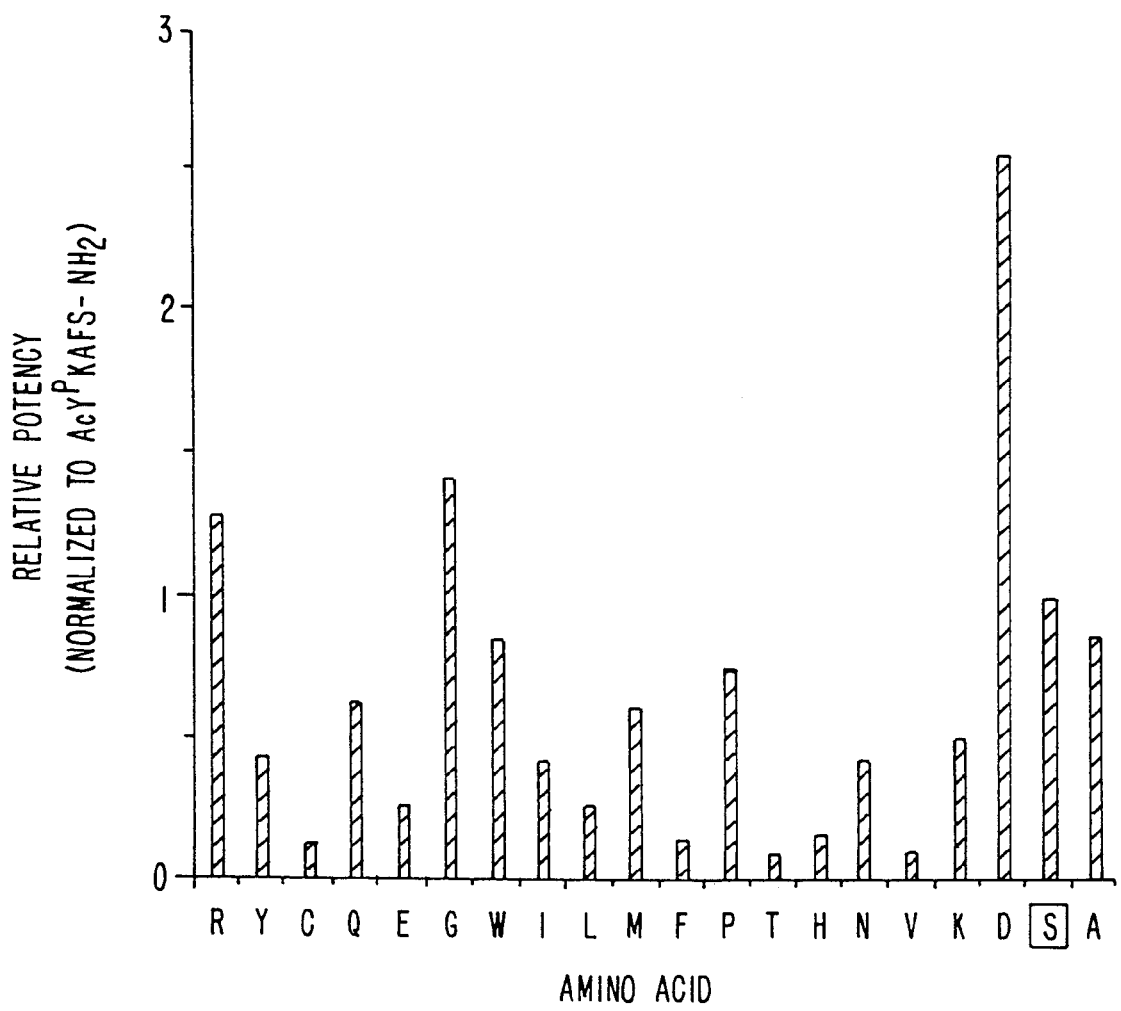
FIG. 6 shows the binding affinity (IC$_{50}$) for peptides having substitutions of the amino acid at the +4 position following the phosphotyrosine (SEQ ID NO:11). Binding potencies are provided relative to that of the naturally occurring amino acid (S) (SEQ ID NO:7).

To identify receptor peptides for use in STAT6 binding assays, a peptide selection scheme was employed. The starting points for the experiment was two docking sites for STAT6 which are present in the IL-4 receptor (FIG. 2). Each of the four amino acids which immediately follow the phosphotyrosine were substituted with each of nineteen different amino acids (total of 76 peptides prepared). The peptides used in the assay were protected with an acetyl group on the amino terminus and an amide group on the carboxyl terminus. The ability of the peptides to inhibit STAT6 binding to STAT6 binding sites on DNA was tested using a gel shift assay. STAT6 binding sites and binding assays are described in U.S. Pat. Nos. 5,591,825, 5,639,858 and 5,710,266.

Results for amino acid substitutions at positions 1–4 are shown in FIGS. 3–6, respectively. From these experiments, we determined that preferred residues are as shown in Table 7.

TABLE 7

Preferred Residues from Peptide SAR

| | |
|---|---|
| $Y^P + 1$ | Strong preference for V (R, I, M are also preferred). All amino acids except G and P are tolerated at this position. |
| $Y^P + 2$ | Preference for P and S. Other amino acids are tolerated at this position. |
| $Y^P + 3$ | Strong preference for W and Y (H and L are also preferred). No other amino acids are tolerated at this position. |
| $Y^P + 4$ | Preference for D and G. Other amino acids are tolerated at this position. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of screening for modulators of STAT4 binding to a STAT4 receptor, the method comprising:

incubating a reaction mixture comprising a STAT4 polypeptide, a potential binding modulator, and a receptor peptide which comprises an amino acid sequence selected from the group consisting of:

YLPZ$_3$ (SEQ ID NO:64), wherein Z$_3$ is selected from the group consisting of Q, H, N, and W; and

GYDMPHVL (SEQ ID NO:4);

wherein the tyrosine is phosphorylated; and determining whether the binding of the STAT4 polypeptide to the receptor peptide is increased or decreased in comparison to an assay which lacks the potential binding modulator.

2. The method of claim 1, wherein the receptor peptide comprises an amino acid sequence selected from the group consisting of YLPZ$_3$N (SEQ ID NO:14) and GYLPZ$_3$ (SEQ ID NO:15).

3. The method of claim 2, wherein the peptide comprises an amino acid sequence GYLPZ$_3$NID (SEQ ID NO:3).

4. The method of claim 3, wherein the amino acid sequence is selected from the group consisting of SHEGYLPQNID (SEQ ID NO:18), SHEGYLPHNID (SEQ ID NO:19), SHEGYLPNNID (SEQ ID NO:20), and SHEGYLPWNID) (SEQ ID NO:21).

5. The method of claim 1, wherein the receptor peptide is immobilized on a solid support.

6. The method of claim 5, wherein the binding of the STAT4 polypeptide to the receptor peptide is detected by contacting the STAT4 polypeptide with a detection moiety which binds to the STAT4 polypeptide and comprises a detectable label.

7. The method of claim 6, wherein the STAT4 polypeptide is preincubated with the detection moiety prior to incubating the receptor peptide with the STAT4 polypeptide.

8. The method of claim 5, wherein the binding of the STAT4 polypeptide to the receptor peptide is detected by contacting the STAT4 polypeptide with a primary antibody which binds to the STAT4 polypeptide, and contacting the primary antibody with a detection moiety which binds to the primary antibody and comprises a detectable label.

9. The method of claim 8, wherein the primary antibody is preincubated with the detection moiety prior to incubating the primary antibody with the STAT4 polypeptide.

10. The method of claim 1, wherein the STAT4 polypeptide is immobilized on a solid support.

11. The method of claim 10, wherein the STAT4 polypeptide is immobilized by noncovalent interaction with the solid support.

12. The method of claim 11, wherein the STAT4 polypeptide comprises a polyhistidine sequence and the solid support comprises $Ni^{2+}$.

13. The method of claim 11, wherein the STAT4 polypeptide comprises a hydrophobic surface and the STAT4 polypeptide is immobilized by hydrophobic interaction.

14. The method of claim 10, wherein the STAT4 polypeptide is immobilized by covalent attachment to the solid support.

15. The method of claim 10, wherein the receptor peptide is detected by contacting the receptor peptide with a detection moiety which binds to the receptor peptide and comprises a detectable label.

16. The method of claim 15, wherein the receptor peptide is preincubated with the detection moiety prior to incubating the receptor peptide with the STAT4 polypeptide.

17. The method of claim 15, wherein the receptor peptide comprises a tag to which the detection moiety binds.

18. The method of claim 15, wherein the detection moiety comprises an antibody which binds to the receptor peptide.

19. The method wherein the detection moiety binds indirectly to the receptor peptide.

20. The method of claim 19, wherein the receptor peptide is contacted with a primary antibody which binds to the receptor peptide, and the primary antibody is contacted with a secondary antibody which comprises the detection moiety.

21. The method of claim 20, wherein the primary antibody is preincubated with the detection moiety prior to contacting the primary antibody with the receptor peptide.

* * * * *

SEQUENCE LISTING (1) GENERAL INFORMATION:

(iii) NUMBER OF SEQUENCES: 64

(2) INFORMATION FOR SEQ ID NO: 1:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Tyr or phosphotyrosine"

(ix) FEATURE:
        (A) NAME/KEY: Modified-site
        (B) LOCATION: 2
        (D) OTHER INFORMATION: /product= "OTHER"
            /note= "Xaa = Lys, Val, Arg, Ile, Met or
            a nonnatural amino acid such as
            tert-butyl glycine, Nva,
            cyclohexylalanine or allothreonine"

(ix) FEATURE:
        (A) NAME/KEY: Modified-site
        (B) LOCATION: 3
        (D) OTHER INFORMATION: /product= "OTHER"
            /note= "Xaa = Pro, Ala or Ser"

(ix) FEATURE:
        (A) NAME/KEY: Modified-site
        (B) LOCATION: 4
        (D) OTHER INFORMATION: /product= "OTHER"
            /note= "Xaa = Trp, Tyr, Phe, His, Leu or
            a nonnatural aromatic amino acid such as
            p-iodophenylalanine, 1-naphthylalanine,
            benzothiophenylalanine, 3-iodotyrosine,
            p-chlorophenylalanine,
            m-trifluoromethylphenylalanine or
            o-chlorophenylalanine"

(xi) SEQUENCE DESCRIPTION: SEQ ID NO: 1:

Xaa Xaa Xaa Xaa
1

(2) INFORMATION FOR SEQ ID NO: 2:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Tyr or phosphotyrosine"

(xi) SEQUENCE DESCRIPTION: SEQ ID NO: 2:

Xaa Lys Pro Phe
1

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Tyr or phosphotyrosine"

(ix) FEATURE:
        (A) NAME/KEY: Modified-site
        (B) LOCATION: 5
        (D) OTHER INFORMATION: /product= "OTHER"
            /note= "Xaa = Gln, His, Asn or Trp"

(xi) SEQUENCE DESCRIPTION: SEQ ID NO: 3:

Gly Xaa Leu Pro Xaa Asn Ile Asp
1               5

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Tyr or phosphotyrosine"

(xi) SEQUENCE DESCRIPTION: SEQ ID NO: 4:

Gly Xaa Asp Met Pro His Val Leu
1               5

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /product= "OTHER"
            /note= "Xaa = phosphotyrosine"

(xi) SEQUENCE DESCRIPTION: SEQ ID NO: 5:

Ala Ser Ser Gly Glu Glu Gly Xaa Lys Pro Phe Gln Asp Leu Ile
1               5                   10                  15

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear

```
        (ii) MOLECULE TYPE: peptide (ix) FEATURE:
             (A) NAME/KEY: Modified-site
             (B) LOCATION: 8
             (D) OTHER INFORMATION: /product= "OTHER"
                 /note= "Xaa = phosphotyrosine"

(xi) SEQUENCE DESCRIPTION: SEQ ID NO: 6:

Gly Pro Pro Gly Glu Ala Gly Xaa Lys Ala Phe Ser Ser Leu Leu
1               5                   10                  15

(2) INFORMATION FOR SEQ ID NO: 7:

(i) SEQUENCE CHARACTERISTICS:
             (A) LENGTH: 5 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                 /note= "Xaa = acetylated
                 phosphotyrosine"

(ix) FEATURE:
             (A) NAME/KEY: Modified-site
             (B) LOCATION: 5
             (D) OTHER INFORMATION: /product= "OTHER"
                 /note= "Xaa = serinamide"

(xi) SEQUENCE DESCRIPTION: SEQ ID NO: 7:

Xaa Lys Ala Phe Xaa
1               5

(2) INFORMATION FOR SEQ ID NO: 8:

(i) SEQUENCE CHARACTERISTICS:
             (A) LENGTH: 5 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                 /note= "Xaa = acetylated
                 phosphotyrosine"

(ix) FEATURE:
             (A) NAME/KEY: Modified-site
             (B) LOCATION: 5
             (D) OTHER INFORMATION: /product= "OTHER"
                 /note= "Xaa = serinamide"

(xi) SEQUENCE DESCRIPTION: SEQ ID NO: 8:

Xaa Xaa Ala Phe Xaa
1               5

(2) INFORMATION FOR SEQ ID NO: 9:

(i) SEQUENCE CHARACTERISTICS:
             (A) LENGTH: 5 amino acids
             (B) TYPE: amino acid
             (C) STRANDEDNESS: <Unknown>
```

(D) TOPOLOGY: linear (ii) MOLECULE TYPE: peptide (ix) FEATURE:
                    (A) NAME/KEY: Modified-site
                    (B) LOCATION: 1
                    (D) OTHER INFORMATION: /product= "OTHER"
                        /note= "Xaa = acetylated
                        phosphotyrosine"

(ix) FEATURE:
                    (A) NAME/KEY: Modified-site
                    (B) LOCATION: 5
                    (D) OTHER INFORMATION: /product= "OTHER"
                        /note= "serinamide"

(xi) SEQUENCE DESCRIPTION: SEQ ID NO: 9:

Xaa Lys Xaa Phe Xaa
 1               5

(2) INFORMATION FOR SEQ ID NO: 10:

(i) SEQUENCE CHARACTERISTICS:
                    (A) LENGTH: 5 amino acids
                    (B) TYPE: amino acid
                    (C) STRANDEDNESS: <Unknown>
                    (D) TOPOLOGY: linear (ii) MOLECULE TYPE: peptide (ix) FEATURE:
                    (A) NAME/KEY: Modified-site
                    (B) LOCATION: 1
                    (D) OTHER INFORMATION: /product= "OTHER"
                        /note= "Xaa = acetylated
                        phosphotyrosine"

(ix) FEATURE:
                    (A) NAME/KEY: Modified-site
                    (B) LOCATION: 5
                    (D) OTHER INFORMATION: /product= "OTHER"
                        /note= "Xaa = serinamide"

(xi) SEQUENCE DESCRIPTION: SEQ ID NO: 10:

Xaa Lys Ala Xaa Xaa
 1               5

(2) INFORMATION FOR SEQ ID NO: 11:

(i) SEQUENCE CHARACTERISTICS:
                    (A) LENGTH: 5 amino acids
                    (B) TYPE: amino acid
                    (C) STRANDEDNESS: <Unknown>
                    (D) TOPOLOGY: linear (ii) MOLECULE TYPE: peptide (ix) FEATURE:
                    (A) NAME/KEY: Modified-site
                    (B) LOCATION: 1
                    (D) OTHER INFORMATION: /product= "OTHER"
                        /note= "Xaa = acetylated
                        phosphotyrosine"

(ix) FEATURE:
                    (A) NAME/KEY: Modified-site
                    (B) LOCATION: 5
                    (D) OTHER INFORMATION: /product= "OTHER"
                        /note= "Xaa = any amidated amino acid"

(xi) SEQUENCE DESCRIPTION: SEQ ID NO: 11:

Xaa Lys Ala Phe Xaa
 1               5

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 2
        (D) OTHER INFORMATION: /product= "OTHER"
            /note= "Xaa = any natural amino acid
            except Ala"

(ix) FEATURE:
        (A) NAME/KEY: Modified-site
        (B) LOCATION: 5
        (D) OTHER INFORMATION: /product= "OTHER"
            /note= "Xaa = serinamide"

(xi) SEQUENCE DESCRIPTION: SEQ ID NO: 12:

Xaa Xaa Ala Phe Xaa
1            5

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 3
        (D) OTHER INFORMATION: /product= "OTHER"
            /note= "Xaa = any natural amino acid
            except Phe"

(ix) FEATURE:
        (A) NAME/KEY: Modified-site
        (B) LOCATION: 5
        (D) OTHER INFORMATION: /product= "OTHER"
            /note= "Xaa = serinamide"

(xi) SEQUENCE DESCRIPTION: SEQ ID NO: 13:

Xaa Lys Xaa Phe Xaa
1            5

(2) INFORMATION FOR SEQ ID NO: 14:

(i) SEQUENCE CHARACTERISTICS:
        (A) LENGTH: 5 amino acids
        (B) TYPE: amino acid (C) STRANDEDNESS: <Unknown>
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /product= "OTHER"
        /note= "Xaa = Tyr or phosphotyrosine"

(ix) FEATURE:
    (A) NAME/KEY: Modified-site
    (B) LOCATION: 4
    (D) OTHER INFORMATION: /product= "OTHER"
        /note= "Xaa = Gln, His, Asn or Trp"

(xi) SEQUENCE DESCRIPTION: SEQ ID NO: 14:

Xaa Leu Pro Xaa Asn
1               5

(2) INFORMATION FOR SEQ ID NO: 15:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Tyr or phosphotyrosine"

(ix) FEATURE:
        (A) NAME/KEY: Modified-site
        (B) LOCATION: 5
        (D) OTHER INFORMATION: /product= "OTHER"
            /note= "Xaa = Gln, His, Asn or Trp"

(xi) SEQUENCE DESCRIPTION: SEQ ID NO: 15:

Gly Xaa Leu Pro Xaa
1               5

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = Tyr or phosphotyrosine"

(xi) SEQUENCE DESCRIPTION: SEQ ID NO: 16:

Gly Xaa Leu Asp Met Pro His Val Leu
1               5

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS: <Unknown>

(D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Tyr or phosphotyrosine"

(xi) SEQUENCE DESCRIPTION: SEQ ID NO: 17:

Glu Gly Xaa Val Pro Trp Gln Asp Leu Ile
1               5                   10

(2) INFORMATION FOR SEQ ID NO: 18:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = Tyr or phosphotyrosine"

(xi) SEQUENCE DESCRIPTION: SEQ ID NO: 18:

Ser His Glu Gly Xaa Leu Pro Gln Asn Ile Asp
1               5                   10

(2) INFORMATION FOR SEQ ID NO: 19:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = Tyr or phosphotyrosine"

(xi) SEQUENCE DESCRIPTION: SEQ ID NO: 19:

Ser His Glu Gly Xaa Leu Pro His Asn Ile Asp
1               5                   10

(2) INFORMATION FOR SEQ ID NO: 20:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = Tyr or phosphotyrosine"

(xi) SEQUENCE DESCRIPTION: SEQ ID NO: 20:

Ser His Glu Gly Xaa Leu Pro Asn Asn Ile Asp (2) INFORMATION FOR SEQ ID NO: 21:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = Tyr or phosphotyrosine"

(xi) SEQUENCE DESCRIPTION: SEQ ID NO: 21:

Ser His Glu Gly Xaa Leu Pro Trp Asn Ile Asp
1               5                   10

(2) INFORMATION FOR SEQ ID NO: 22:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = phosphotyrosine"

(xi) SEQUENCE DESCRIPTION: SEQ ID NO: 22:

Ser His Glu Gly Xaa Leu Pro Ser Asn Ile Asp
1               5                   10

(2) INFORMATION FOR SEQ ID NO: 23:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = phosphotyrosine"

(xi) SEQUENCE DESCRIPTION: SEQ ID NO: 23:

Ser His Glu Gly Xaa Leu Pro Gln Asn Ile Asp
1               5                   10

(2) INFORMATION FOR SEQ ID NO: 24:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide

```
        (ix) FEATURE:
              (A) NAME/KEY: Modified-site
              (B) LOCATION: 5
              (D) OTHER INFORMATION: /product= "OTHER"
                  /note= "Xaa = phosphotyrosine"

(xi) SEQUENCE DESCRIPTION: SEQ ID NO: 24:

Ser His Glu Gly Xaa Leu Pro His Asn Ile Asp
1                5                   10

(2) INFORMATION FOR SEQ ID NO: 25:

(i) SEQUENCE CHARACTERISTICS:
              (A) LENGTH: 11 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 5
              (D) OTHER INFORMATION: /product= "OTHER"
                  /note= "Xaa = phosphotyrosine"

(xi) SEQUENCE DESCRIPTION: SEQ ID NO: 25:

Ser His Glu Gly Xaa Leu Pro Asn Asn Ile Asp
1                5                   10

(2) INFORMATION FOR SEQ ID NO: 26:

(i) SEQUENCE CHARACTERISTICS:
              (A) LENGTH: 11 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 5
              (D) OTHER INFORMATION: /product= "OTHER"
                  /note= "Xaa = phosphotyrosine"

(xi) SEQUENCE DESCRIPTION: SEQ ID NO: 26:

Ser His Glu Gly Xaa Leu Pro Trp Asn Ile Asp
1                5                   10

(2) INFORMATION FOR SEQ ID NO: 27:

(i) SEQUENCE CHARACTERISTICS:
              (A) LENGTH: 4 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                  /note= "Xaa = Tyr or phosphotyrosine"

(ix) FEATURE:
              (A) NAME/KEY: Modified-site
              (B) LOCATION: 2
              (D) OTHER INFORMATION: /product= "OTHER"
                  /note= "Xaa = Lys, Val, Arg, Ile, Met or
                  a nonnatural amino acid such as
                  tert-butyl glycine, Nva,
```

```
                  cyclohexylalanine or allothreonine"

(ix) FEATURE:
            (A) NAME/KEY: Modified-site
            (B) LOCATION: 3
            (D) OTHER INFORMATION: /product= "OTHER"
                /note= "Xaa = Pro, Ala or Ser"

(ix) FEATURE:
            (A) NAME/KEY: Modified-site
            (B) LOCATION: 4
            (D) OTHER INFORMATION: /product= "OTHER"
                /note= "Xaa = Trp, Tyr, Phe, His, Leu or
                a nonnatural aromatic amino acid such as
                p-iodophenylalanine, 1-naphthylalanine,
                benzothiophenylalanine, 3-iodotyrosine,
                p-chlorophenylalanine,
                o-trifluoromethylphenylalanine or
                o-chlorophenylalanine"

(xi) SEQUENCE DESCRIPTION: SEQ ID NO: 27:

Xaa Xaa Xaa Xaa
1

(2) INFORMATION FOR SEQ ID NO: 28:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = Tyr or phosphotyrosine"

(ix) FEATURE:
            (A) NAME/KEY: Modified-site
            (B) LOCATION: 2
            (D) OTHER INFORMATION: /product= "OTHER"
                /note= "Xaa = Lys, Val, Arg, Ile, Met or
                a nonnatural amino acid such as
                tert-butyl glycine, Nva,
                cyclohexylalanine or allothreonine"

(ix) FEATURE:
            (A) NAME/KEY: Modified-site
            (B) LOCATION: 4
            (D) OTHER INFORMATION: /product= "OTHER"
                /note= "Xaa = Trp, Tyr, Phe, His or Leu (xi) SEQUENCE DESCRIPTION: SEQ ID NO: 28:

Xaa Xaa Xaa Xaa
1

(2) INFORMATION FOR SEQ ID NO: 29:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /note= "Xaa = any amino acid except
                Gly or Pro"
```

```
        (ix) FEATURE:
              (A) NAME/KEY: Modified-site
              (B) LOCATION: 4
              (D) OTHER INFORMATION: /product= "OTHER"
                    /note= "Xaa = Trp, Tyr, Phe, His or Leu (xi) SEQUENCE DESCRIPTION: SEQ ID NO: 29:

Xaa Xaa Xaa Xaa
1

(2) INFORMATION FOR SEQ ID NO: 30:

(i) SEQUENCE CHARACTERISTICS:
              (A) LENGTH: 5 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                    /note= "Xaa = Tyr or phosphotyrosine"

(ix) FEATURE:
              (A) NAME/KEY: Modified-site
              (B) LOCATION: 2
              (D) OTHER INFORMATION: /product= "OTHER"
                    /note= "Xaa = Lys, Val, Arg, Ile, Met or
                    a nonnatural amino acid such as
                    tert-butyl glycine, Nva,
                    cyclohexylalanine or allothreonine"

(ix) FEATURE:
              (A) NAME/KEY: Modified-site
              (B) LOCATION: 3
              (D) OTHER INFORMATION: /product= "OTHER"
                    /note= "Xaa = Pro, Ala or Ser"

(ix) FEATURE:
              (A) NAME/KEY: Modified-site
              (B) LOCATION: 4
              (D) OTHER INFORMATION: /product= "OTHER"
                    /note= "Xaa = Trp, Tyr, Phe, His, Leu or
                    a nonnatural aromatic amino acid such as
                    p-iodophenylalanine, 1-naphthylalanine,
                    benzothiophenylalanine, 3-iodotyrosine,
                    p-chlorophenylalanine,
                    m-trifluoromethylphenylalanine or
                    o-chlorophenylalanine"

(ix) FEATURE:
              (A) NAME/KEY: Modified-site
              (B) LOCATION: 5
              (D) OTHER INFORMATION: /product= "OTHER"
                    /note= "Xaa = Asp or Gly"

(xi) SEQUENCE DESCRIPTION: SEQ ID NO: 30:

Xaa Xaa Xaa Xaa Xaa
1               5

(2) INFORMATION FOR SEQ ID NO: 31:

(i) SEQUENCE CHARACTERISTICS:
              (A) LENGTH: 10 amino acids
              (B) TYPE: amino acid
              (C) STRANDEDNESS: <Unknown>
              (D) TOPOLOGY: linear (ii) MOLECULE TYPE: peptide (ix) FEATURE:
```

(A) NAME/KEY: Modified-site
        (B) LOCATION: 3
        (D) OTHER INFORMATION: /product= "OTHER"
            /note= "Xaa = Tyr or phosphotyrosine"

(ix) FEATURE:
        (A) NAME/KEY: Modified-site
        (B) LOCATION: 6
        (D) OTHER INFORMATION: /product= "OTHER"
            /note= "Xaa = a nonnatural aromatic
            amino acid such as p-iodophenylalanine,
            1-naphthylalanine,
            benzothiophenylalanine, 3-iodotyrosine,
            p-chlorophenylalanine,
            o-trifluoromethylphenylalanine or
            o-chlorophenylalanine"

(xi) SEQUENCE DESCRIPTION: SEQ ID NO: 31:

Glu Gly Xaa Lys Pro Xaa Gln Asp Leu Ile
1               5                   10

(2) INFORMATION FOR SEQ ID NO: 32:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Tyr or phosphotyrosine"

(ix) FEATURE:
        (A) NAME/KEY: Modified-site
        (B) LOCATION: 4
        (D) OTHER INFORMATION: /product= "OTHER"
            /note= "Xaa = a nonnatural amino acid
            such as tert-butyl glycine, Nva,
            cyclohexylalanine or allothreonine"

(xi) SEQUENCE DESCRIPTION: SEQ ID NO: 32:

Glu Gly Xaa Xaa Pro Gln Trp Asp Leu Ile
1               5                   10

(2) INFORMATION FOR SEQ ID NO: 33:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 4
        (D) OTHER INFORMATION: /product= "OTHER"
            /note= "Xaa = tryptophanamide"

(xi) SEQUENCE DESCRIPTION: SEQ ID NO: 33:

Xaa Val Pro Xaa

```
(2) INFORMATION FOR SEQ ID NO: 34:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 5
        (D) OTHER INFORMATION: /product= "OTHER"
            /note= "Xaa = glutaminamide"

(xi) SEQUENCE DESCRIPTION: SEQ ID NO: 34:

Xaa Val Pro Trp Xaa
1               5

(2) INFORMATION FOR SEQ ID NO: 35:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 4
        (D) OTHER INFORMATION: /product= "OTHER"
            /note= "Xaa = phenylaninamide"

(xi) SEQUENCE DESCRIPTION: SEQ ID NO: 35:

Xaa Lys Pro Xaa
1

(2) INFORMATION FOR SEQ ID NO: 36:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
```

```
        (A) NAME/KEY: Modified-site
        (B) LOCATION: 4
        (D) OTHER INFORMATION: /product= "OTHER"
            /note= "Xaa = tryptophanamide"

(xi) SEQUENCE DESCRIPTION: SEQ ID NO: 36:

Xaa Val Pro Xaa
1

(2) INFORMATION FOR SEQ ID NO: 37:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = acetylated
            phosphotyrosine"

(ix) FEATURE:
        (A) NAME/KEY: Modified-site
        (B) LOCATION: 5
        (D) OTHER INFORMATION: /product= "OTHER"
            /note= "Xaa = glutaminamide"

(xi) SEQUENCE DESCRIPTION: SEQ ID NO: 37:

Xaa Val Pro Trp Xaa
1               5

(2) INFORMATION FOR SEQ ID NO: 38:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = phosphotyrosine"

(xi) SEQUENCE DESCRIPTION: SEQ ID NO: 38:

Glu Gly Xaa Val Pro Trp Gln Asp Leu Ile
1               5                   10

(2) INFORMATION FOR SEQ ID NO: 39:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = Tyr or phosphotyrosine"

(ix) FEATURE:
```

-continued (A) NAME/KEY: Modified-site
        (B) LOCATION: 6
        (D) OTHER INFORMATION: /product= "OTHER"
            /note= "Xaa = a nonnatural aromatic
            amino acid such as p-iodophenylalanine,
            1-naphthylalanine,
            benzothiophenylalanine, 3-iodotyrosine,
            p-chlorophenylalanine,
            m-trifluoromethylphenylalanine or
            o-chlorophenylalanine"

(xi) SEQUENCE DESCRIPTION: SEQ ID NO: 39:

Glu Gly Xaa Lys Pro Xaa Gln Asp Leu Ile
1               5                   10

(2) INFORMATION FOR SEQ ID NO: 40:

(i) SEQUENCE CHARACTERISTICS:
        (A) LENGTH: 201 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1..97
        (D) OTHER INFORMATION: /product= "OTHER"
            /note= "Gly at positions 1-97 may be
            present or absent"

(ix) FEATURE:
        (A) NAME/KEY: Modified-site
        (B) LOCATION: 105..201
        (D) OTHER INFORMATION: /product= "OTHER"
            /note= "Gly at positions 105-201 may be
            present or absent"

(xi) SEQUENCE DESCRIPTION: SEQ ID NO: 40:

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
            85                  90                  95

Gly Gly Gly Gly Pro Gly Gly Gly Gly Gly Gly Gly Gly Gly Gly
        100                 105                 110

Gly Gly Gly Gly Gly Gly Gly Gly Gly Gly Gly Gly Gly Gly Gly
    115                 120                 125

Gly Gly Gly Gly Gly Gly Gly Gly Gly Gly Gly Gly Gly Gly Gly
130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
        180                 185                 190

Gly Gly Gly Gly Gly Gly Gly Gly Gly
        195                 200

(2) INFORMATION FOR SEQ ID NO: 41:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = phosphotyrosine"

(xi) SEQUENCE DESCRIPTION: SEQ ID NO: 41:

Gly Xaa Asp Lys Pro His Val Leu
1               5

(2) INFORMATION FOR SEQ ID NO: 42:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = phosphotyrosine"

(xi) SEQUENCE DESCRIPTION: SEQ ID NO: 42:

Ser Phe Gly Xaa Asp Lys Pro His Val Leu
1               5                   10

(2) INFORMATION FOR SEQ ID NO: 43:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "OTHER"
            /note= "Xaa = phosphotyrosine"

(xi) SEQUENCE DESCRIPTION: SEQ ID NO: 43:

Gly Xaa Ala Lys Pro His Val Leu
1               5

(2) INFORMATION FOR SEQ ID NO: 44:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide

```
    (ix) FEATURE:
         (A) NAME/KEY: Modified-site
         (B) LOCATION: 2
         (D) OTHER INFORMATION: /product= "OTHER"
             /note= "Xaa = phosphotyrosine"

(xi) SEQUENCE DESCRIPTION: SEQ ID NO: 44:

Gly Xaa Asp Ala Pro His Val Leu
1               5

(2) INFORMATION FOR SEQ ID NO: 45:

(i) SEQUENCE CHARACTERISTICS:
         (A) LENGTH: 8 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = phosphotyrosine"

(xi) SEQUENCE DESCRIPTION: SEQ ID NO: 45:

Gly Xaa Asp Lys Ala His Val Leu
1               5

(2) INFORMATION FOR SEQ ID NO: 46:

(i) SEQUENCE CHARACTERISTICS:
         (A) LENGTH: 8 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = phosphotyrosine"

(xi) SEQUENCE DESCRIPTION: SEQ ID NO: 46:

Gly Xaa Asp Met Pro His Val Leu
1               5

(2) INFORMATION FOR SEQ ID NO: 47:

(i) SEQUENCE CHARACTERISTICS:
         (A) LENGTH: 9 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Modified-site
         (B) LOCATION: 2
         (D) OTHER INFORMATION: /product= "OTHER"
             /note= "Xaa = phosphotyrosine"

(xi) SEQUENCE DESCRIPTION: SEQ ID NO: 47:

Gly Xaa Lys Pro Phe Gln Asp Leu Ile
1               5
```

(2) INFORMATION FOR SEQ ID NO: 48:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 2
        (D) OTHER INFORMATION: /product= "OTHER"
            /note= "Xaa = Ile or Val"

(xi) SEQUENCE DESCRIPTION: SEQ ID NO: 48:

Xaa Xaa Asn Xaa
1

(2) INFORMATION FOR SEQ ID NO: 49:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(ix) FEATURE:
        (A) NAME/KEY: Modified-site
        (B) LOCATION: 2
        (D) OTHER INFORMATION: /product= "OTHER"
            /note= "Xaa = Leu or Ile"

(xi) SEQUENCE DESCRIPTION: SEQ ID NO: 49:

Xaa Xaa Ile Pro
1

(2) INFORMATION FOR SEQ ID NO: 50:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 50:

Xaa Glu Glu Ile
1

(2) INFORMATION FOR SEQ ID NO: 51:

```
        (i) SEQUENCE CHARACTERISTICS:
             (A) LENGTH: 4 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                  /note= "Xaa = phosphotyrosine"

(xi) SEQUENCE DESCRIPTION: SEQ ID NO: 51:

Xaa Xaa Asn Xaa
1

(2) INFORMATION FOR SEQ ID NO: 52:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                  /note= "Xaa = phosphotyrosine"

(ix) FEATURE:
             (A) NAME/KEY: Modified-site
             (B) LOCATION: 3
             (D) OTHER INFORMATION: /product= "OTHER"
                  /note= "Xaa = phosphotyrosine"

(xi) SEQUENCE DESCRIPTION: SEQ ID NO: 52:

Xaa Ile Xaa Val
1

(2) INFORMATION FOR SEQ ID NO: 53:

(i) SEQUENCE CHARACTERISTICS:
             (A) LENGTH: 6 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /product= "OTHER"
                  /note= "Xaa = phosphotyrosine"

(xi) SEQUENCE DESCRIPTION: SEQ ID NO: 53:

Xaa Ile Thr Pro Leu Pro
1               5

(2) INFORMATION FOR SEQ ID NO: 54:

(i) SEQUENCE CHARACTERISTICS:
             (A) LENGTH: 6 amino acids
             (B) TYPE: amino acid
             (C) STRANDEDNESS: <Unknown>
             (D) TOPOLOGY: linear
```

```
    (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 54:

Xaa Thr Ala Val Gln Pro
1               5

(2) INFORMATION FOR SEQ ID NO: 55:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 55:

Xaa Val Pro Met
1

(2) INFORMATION FOR SEQ ID NO: 56:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 56:

Xaa Xaa Xaa Leu
1

(2) INFORMATION FOR SEQ ID NO: 57:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 57:

Xaa Met Ala Pro
1
```

(2) INFORMATION FOR SEQ ID NO: 58:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 58:

Xaa Met Asn Met
1

(2) INFORMATION FOR SEQ ID NO: 59:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 59:

Xaa Met Asp Met
1

(2) INFORMATION FOR SEQ ID NO: 60:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = phosphotyrosine"

(xi) SEQUENCE DESCRIPTION: SEQ ID NO: 60:

Xaa Met Xaa Met
1

(2) INFORMATION FOR SEQ ID NO: 61:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site

```
        (B) LOCATION: 1
        (D) OTHER INFORMATION: /product= "OTHER"
             /note= "Xaa = Tyr or phosphotyrosine"

(ix) FEATURE:
        (A) NAME/KEY: Modified-site
        (B) LOCATION: 2
        (D) OTHER INFORMATION: /product= "OTHER"
             /note= "Xaa = Lys, Val, Arg, Ile, Met or
             a nonnatural amino acid"

(ix) FEATURE:
        (A) NAME/KEY: Modified-site
        (B) LOCATION: 3
        (D) OTHER INFORMATION: /product= "OTHER"
             /note= "Xaa = Pro, Ala or Ser"

(ix) FEATURE:
        (A) NAME/KEY: Modified-site
        (B) LOCATION: 4
        (D) OTHER INFORMATION: /product= "OTHER"
             /note= "Xaa = Trp, Tyr, Phe, His, Leu or
             a nonnatural aromatic amino acid"

(xi) SEQUENCE DESCRIPTION: SEQ ID NO: 61:

Xaa Xaa Xaa Xaa
1

(2) INFORMATION FOR SEQ ID NO: 62:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
             /note= "Xaa = Tyr or phosphotyrosine"

(ix) FEATURE:
        (A) NAME/KEY: Modified-site
        (B) LOCATION: 2
        (D) OTHER INFORMATION: /product= "OTHER"
             /note= "Xaa = Lys, Val, Arg, Ile, Met or
             a nonnatural amino acid"

(ix) FEATURE:
        (A) NAME/KEY: Modified-site
        (B) LOCATION: 3
        (D) OTHER INFORMATION: /product= "OTHER"
             /note= "Xaa = Pro, Ala or Ser"

(ix) FEATURE:
        (A) NAME/KEY: Modified-site
        (B) LOCATION: 4
        (D) OTHER INFORMATION: /product= "OTHER"
             /note= "Xaa = Trp, Tyr, Phe, His, Leu or
             a nonnatural aromatic amino acid"

(ix) FEATURE:
        (A) NAME/KEY: Modified-site
        (B) LOCATION: 5
        (D) OTHER INFORMATION: /product= "OTHER"
             /note= "Xaa = Asp or Gly"

(xi) SEQUENCE DESCRIPTION: SEQ ID NO: 62:

Xaa Xaa Xaa Xaa Xaa
1               5

(2) INFORMATION FOR SEQ ID NO: 63:
```

-continued

```
        (i) SEQUENCE CHARACTERISTICS:
              (A) LENGTH: 4 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                  /note= "Xaa = Tyr or phosphotyrosine"

(xi) SEQUENCE DESCRIPTION: SEQ ID NO: 63:

Xaa Val Pro Trp
1

(2) INFORMATION FOR SEQ ID NO: 64:

(i) SEQUENCE CHARACTERISTICS:
              (A) LENGTH: 4 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                  /note= "Xaa = Tyr or phosphotyrosine"

(ix) FEATURE:
              (A) NAME/KEY: Modified-site
              (B) LOCATION: 4
              (D) OTHER INFORMATION: /product= "OTHER"
                  /note= "Xaa = Gln, His, Asn or Trp"

(xi) SEQUENCE DESCRIPTION: SEQ ID NO: 64:

Xaa Leu Pro Xaa
1
```